United States Patent
Fink et al.

(10) Patent No.: US 7,384,748 B2
(45) Date of Patent: Jun. 10, 2008

(54) COMPOSITIONS AND METHODS FOR DETECTING AND TREATING MOTOR NEURON DISORDERS

(75) Inventors: John K. Fink, Ann Arbor, MI (US); Shirley Rainer, Sylvania, OH (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/301,524

(22) Filed: Dec. 13, 2005

(65) Prior Publication Data

US 2006/0228724 A1    Oct. 12, 2006

Related U.S. Application Data

(60) Provisional application No. 60/635,459, filed on Dec. 13, 2004.

(51) Int. Cl.
*C12Q 1/68*      (2006.01)
*C12Q 1/00*      (2006.01)
*G01N 33/566*    (2006.01)
*G01N 33/567*    (2006.01)

(52) U.S. Cl. .............................. 435/6; 435/4; 436/501; 436/503; 436/504; 536/24.3

(58) Field of Classification Search .................... None
See application file for complete search history.

(56) References Cited

U.S. PATENT DOCUMENTS

2005/0003390 A1 * 1/2005 Axenovich et al. ............ 435/6

OTHER PUBLICATIONS

Winrow, C. J., et al., "Loss of neuropathy target esterase in mice links organophosphate exposure to hyperactivity," (2003) Nature Genetics 33: 477-485.
Bargal, R., et al., "Identification of the gene causing mucolipidosis type IV," (2000) Nature Genetics 26: 118-123.
Lush, M. J., et al., "Neuropathy target esterase and a homologous Drosophila neurodegeneration-associated mutant protein contain a novel domain conserved from bacteria to man," (1998) Biochem. J. 332: 1-4.
Moser, M., et al., "Placental failure and impaired vasculogenesis result in embryonic lethality for neuropathy target esterase-deficient mice," (2004) Molec. Cell. Biol. 24: 1667-1679.
O'Callaghan, J P. "Neurotoxic esterase: not so toxic?," (2003) Nature Genetics 33: 437-438.

* cited by examiner

*Primary Examiner*—Olga N. Chernyshev
(74) *Attorney, Agent, or Firm*—Casimir Jones S.C.

(57) ABSTRACT

The present invention relates to the NTE proteins and nucleic acids encoding the NTE proteins. The present invention further provides assays for the detection of NTE polymorphisms and mutations associated with disease states, as well as methods of screening for ligands and modulators of NTE proteins.

1 Claim, 10 Drawing Sheets

FIGURE 1- A
SEQ ID NO: 1

```
                        10                    20
30                      40                    50
   0 ATGGAGGCTC CGCTGCAAAC TGGAATGGTG CTTGGCGTGA TGATCGGGGC
  50 CGGAGTGGCG GTGGTGGTCA CGGCCGTGCT CATCCTCCTG GTGGTGCGGA
 100 GGCTGCGAGT GCCAAAAACC CCAGCCCCGG ATGGCCCCCG GTATCGGTTC
 150 CGGAAGAGGG ACAAAGTGCT CTTCTATGGC CGGAAGATTA TGCGGAAGGT
 200 GTCACAATCC ACCTCCTCCC TCGTGGATAC CTCTGTCTCC GCCACCTCCC
 250 GGCCACGCAT GAGGAAGAAA CTGAAGATGC TCAACATTGC CAAGAAGATC
 300 CTGCGCATCC AGAAAGAGAC GCCCACGCTG CAGCGGAAGG AGCCCCCGCC
 350 CGCAGTGCTA GAAGCTGACC TGACCGAGGG CGACCTGGCT AACTCCCATC
 400 TGCCCTCTGA AGTGCTTTAT ATGCTCAAGA ACGTCCGGGT GCTGGGCCAC
 450 TTCGAGAAGC CACTCTTCCT GGAGCTCTGC CGCCACATGG TCTTCCAGCG
 500 GCTGGGCCAG GGTGACTACG TCTTCCGGCC GGGCCAGCCA GATGCCAGCA
 550 TCTACGTGGT GCAGGACGGG CTGCTGGAGC TCTGTCTGCC AGGGCCTGAC
 600 GGGAAGGAGT GTGTGGTGAA GGAAGTGGTT CCTGGGGACA GCGTCAACAG
 650 CCTTCTCAGC ATCCTGGATG TCATCACCGG TCACCAGCAT CCCCAGCGGA
 700 CCGTGTCTGC CCGGGCGGCC CGGGACTCCA CGGTGCTGCG CCTGCCGGTG
 750 GAAGCATTCT CCGCGGTCTT CACCAAGTAC CCGGAGAGCT TGGTGCGGGT
 800 CGTGCAGATC ATCATGGTGC GGCTGCAGCG AGTCACCTTC CTGGCACTGC
 850 ACAACTACCT GGGTCTGACC AATGAGCTCT TCAGCCACGA GATCCAGCCC
 900 CTGCGTCTGT TCCCCAGCCC CGGCCTCCCA ACTCGCACCA GCCTGTGCG
 950 GGGCTCCAAG AGAATGGTCA GCACCTCAGC TACAGACGAG CCCAGGGAGA
1000 CCCCAGGGCG GCCACCCGAT CCCACCGGGG CCCCGCTGCC TGGACCTACA
1050 GGGGACCCTG TGAAGCCCAC ATCCCTGGAA ACCCCCTCGC CCCCTCTGCT
1100 GAGCCGCTGC GTCTCCATGC CAGGGGACAT CTCAGGCTTG CAGGGTGGCC
1150 CCCGCTCCGA CTTCGACATG GCCTATGAGC GTGGCCGGAT CTCCGTGTCC
1200 CTGCAAGAAG AGGCCTCCGG GGGGTCCCTG GCAGCCCCCG CTCGGACCCC
1250 CACTCAGGAG CCTCGTGAGC AGCCGGCAGG CGCCTGTGAA TACAGCTACT
1300 GTGAGGATGA GTCGGCCACT GGTGGCTGCC CTTTCGGGCC CTACCAGGGC
1350 CGCCAGACCA GCAGCATCTT CGAGGCAGCA AAGCAGGAGC TGGCCAAGCT
1400 GATGCGGATT GAGGACCCCT CCCTCCTGAA CAGCAGAGTC TTGCTGCACC
1450 ACGCCAAAGC TGGCACCATC ATTGCCCGCC AGGGAGACCA GGACGTGAGC
1500 CTGCACTTCG TGCTCTGGGG CTGCCTGCAC GTGTACCAGC GCATGATCGA
1550 CAAGGCGGAG GACGTGTGCC TGTTCGTAGC GCAGCCCGGG GAACTGGTGG
1600 GGCAGCTGGC GGTGCTCACT GGCGAACCTC TCATCTTCAC ACTGCGAGCC
1650 CAACGCGACT GCACCTTCCT GCGGATCTCC AAGTCCGACT TCTATGAGAT
1700 CATGCGCGCA CAGCCCAGTG TGGTGCTGAG TGCGGCGCAC ACGGTGGCAG
1750 CCAGGATGTC GCCCTTCGTG CGCCAGATGG ACTTCGCCAT CGACTGGACT
1800 GCAGTGGAGG CGGGACGCGC GCTGTACAGG CAGGGCGACC GCTCCGACTG
1850 CACTTACATC GTGCTCAATG GCGGCTGCG TAGCGTGATC CAGCGAGGCA
1900 GTGGCAAGAA GGAGCTGGTG GGCGAGTACG GCCGCGGCGA CCTCATCGGC
1950 GTGGTGGAGG CACTGACCCG GCAGCCGCGA GCCACGACGG TGCACGCGGT
2000 GCGCGACACG GAGCTGGCCA AGCTTCCCGA GGGCACCTTG GGTCACATCA
2050 AACGCCGGTA CCCGCAGGTC GTGACCCGCC TTATCCACCT ACTGAGCCAG
2100 AAAATTCTAG GAATTTGCA GCAGCTGCAA GGACCCTTCC CAGCAGGCTC
2150 TGGGTTGGGT GTGCCCCCAC ACTCGGAACT CACCAACCCA GCCAGCAACC
2200 TGGCAACTGT GGCAATCCTG CCTGTGTGTG CTGAGGTCCC CATGGTGGCC
2250 TTCACGCTGG AGCTGCAGCA CGCCCTGCAG GCCATCGGTC CGACGCTACT
2300 CCTTAACAGT GACATCATCC GGGCACGCCT GGGGGCCTCC GCACTGGATA
2350 GCATCCAAGA GTTCCGGCTG TCAGGGTGGC TGGCCCAGCA GGAGGATGCA
2400 CACCGTATCG TACTCTACCA GACGGACGCC TCGCTGACGC CCTGGACCGT
```

FIGURE 1 - B

```
2450 GCGCTGCCTG CGACAGGCCG ACTGCATCCT CATTGTGGGC CTGGGGGACC
2500 AGGAGCCTAC CCTCGGCCAG CTGGAGCAGA TGCTGGAGAA CACGGCTGTG
2550 CGCGCCCTTA AGCAGCTAGT CCTGCTCCAC CGAGAGGAGG GCGCGGGCCC
2600 CACGCGCACC GTGGAGTGGC TAAATATGCG CAGCTGGTGC TCGGGGCACC
2650 TGCACCTGCG CTGTCCGCGC CGCCTCTTTT CGCGCCGCAG CCCTGCCAAG
2700 CTGCATGAGC TCTACGAGAA GGTTTTCTCC AGGCGCGCGG ACCGGCACAG
2750 CGACTTCTCC CGCTTGGCGA GGGTGCTCAC GGGGAACACC ATTGCCCTTG
2800 TGCTAGGCGG GGGCGGGGCC AGGGGCTGCT CGCACATCGG AGTACTAAAG
2850 GCATTAGAGG AGGCGGGGGT CCCCGTGGAC CTGGTGGGCG GCACGTCCAT
2900 TGGCTCTTTC ATCGGAGCGT TGTACGCGGA GGAGCGCAGC GCCAGCCGCA
2950 CGAGGCAGCG GGCCCGGGAG TGGGCCAAGA GCATGACTTC GGTGCTGGAA
3000 CCTGTGTTGG ACCTCACGTA CCCAGTCACC TCCAtGTTCA CTGGGTCTGC
3050 CTTTAACCGC AGCATCCATC GGGTCTTCCA GGATAAGCAG ATTGAGGACC
3100 TGTGGCTGCC TTACTTCAAC GTGACCACAG ATATCACCGC CTCAGCCATG
3150 CGAGTCCACA AAGATGGCTC CCTGTGGCGG TACGTGCGCG CCAGCATGAC
3200 GCTGTCGGGC TACCTGCCCC CGCTGTGCGA CCCCAAGGAC GGGCACCTAC
3250 TCATGGATGG CGGCTACATC AACAATCTGC CAGCGGACAT CGCCCGCAGC
3300 ATGGGTGCCA AAACGGTCAT CGCCATTGAC GTGGGGAGCC AGGATGAGAC
3350 GGACCTCAGC ACCTACGGGG ACAGCCTGTC CGGCTGGTGG CTGCTGTGGA
3400 AGCGGCTGAA TCCCTGGGCT GACAAGGTAA AGGTTCCAGA CATGGCTGAA
3450 ATCCAGTCCC GCCTGGCCTA CGTGTCCTGT GTGCGGCAGC TAGAGGTTGT
3500 CAAGTCCAGC TCCTACTGCG AGTACCTGCG CCCGCCCATC GACTGCTTCA
3550 AGACCATGGA CTTTGGGAAG TTCGACCAGA TCTATGATGT GGGCTACCAG
3600 TACGGGAAGG CGGTGTTTGG AGGCTGGAGC CGTGGCAACG TCATTGAGAA
3650 AATGCTCACA GACCGGCGGT CTACAGACCT TAATGAGAGC CGCCGTGCAG
3700 ACGTGCTTGC CTTCCCAAGC TCTGGCTTCA CTGACTTGGC AGAGATTGTG
3750 TCCCGGATTG AGCCCCCCAC GAGCTATGTC TCTGATGGCT GTGCTGACGG
3800 AGAGGAGTCA GATTGTCTGA CAGAGTATGA GGAGGACGCC GGACCCGACT
3850 GCTCGAGGGA TGAAGGGGGG TCCCCCGAGG GCGCAAGCCC CAGCACTGCC
3900 TCCGAGATGG AGGAGGAGAA GTCGATTCTC CGGCAACGAC GCTGTCTGCC
3950 CCAGGAGCCG CCCGGCTCAG CCACAGATGC CTGAGGACCT CGACAGGGGT
4000 CACCCCCTCC CTCCCACCCC TGGACTGGGC TGGGGGTGGC CCCGTGGGGG
4050 TAGCTCACTC CCCCTCCTGC TGCTATGCCT GTGACCCCCG CGGCCCACAC
4100 ACTGGACTGA CCTGCCCTGA GCGGGGATGC AGTGTTGCAC TGATGACTTG
4150 ACCAGCCCCT CCCCAATAA ACTCGCCTCT TGGAAAAAAA AAAAAAAAA
4200 AAAAAAAAAA AAAAAAAAA AAAAA
```

FIGURE 2 - A
SEQ ID NO: 2

```
                              10                    20
30                   40                   50
   0 ATGGAGGCTC CGCTGCAAAC TGGAATGGTG CTTGGCGTGA TGATCGGGGC
  50 CGGAGTGGCG GTGGTGGTCA CGGCCGTGCT CATCCTCCTG GTGGTGCGGA
 100 GGCTGCGAGT GCCAAAAACC CCAGCCCCGG ATGGCCCCCG GTATCGGTTC
 150 CGGAAGAGGG ACAAAGTGCT CTTCTATGGC CGGAAGATTA TGCGGAAGGT
 200 GTCACAATCC ACCTCCTCCC TCGTGGATAC CTCTGTCTCC GCCACCTCCC
 250 GGCCACGCAT GAGGAAGAAA CTGAAGATGC TCAACATTGC CAAGAAGATC
 300 CTGCGCATCC AGAAAGAGAC GCCCACGCTG CAGCGGAAGG AGCCCCCGCC
 350 CGCAGTGCTA GAAGCTGACC TGACCGAGGG CGACCTGGCT AACTCCCATC
 400 TGCCCTCTGA AGTGCTTTAT ATGCTCAAGA ACGTCCGGGT GCTGGGCCAC
 450 TTCGAGAAGC CACTCTTCCT GGAGCTCTGC CGCCACATGG TCTTCCAGCG
 500 GCTGGGCCAG GGTGACTACG TCTTCCGGCC GGGCCAGCCA GATGCCAGCA
 550 TCTACGTGGT GCAGGACGGG CTGCTGGAGC TCTGTCTGCC AGGGCCTGAC
 600 GGGAAGGAGT GTGTGGTGAA GGAAGTGGTT CCTGGGGACA GCGTCAACAG
 650 CCTTCTCAGC ATCCTGGATG TCATCACCGG TCACCAGCAT CCCCAGCGGA
 700 CCGTGTCTGC CCGGGCGGCC CGGGACTCCA CGGTGCTGCG CCTGCCGGTG
 750 GAAGCATTCT CCGCGGTCTT CACCAAGTAC CCGGAGAGCT TGGTGCGGGT
 800 CGTGCAGATC ATCATGGTGC GGCTGCAGCG AGTCACCTTC CTGGCACTGC
 850 ACAACTACCT GGGTCTGACC AATGAGCTCT TCAGCCACGA GATCCAGCCC
 900 CTGCGTCTGT TCCCCAGCCC CGGCCTCCCA ACTCGCACCA GCCCTGTGCG
 950 GGGCTCCAAG AGAATGGTCA GCACCTCAGC TACAGACGAG CCCAGGGAGA
1000 CCCCAGGGCG GCCACCCGAT CCCACCGGGG CCCCGCTGCC TGGACCTACA
1050 GGGGACCCTG TGAAGCCCAC ATCCCTGGAA ACCCCCTCGC CCCCTCTGCT
1100 GAGCCGCTGC GTCTCCATGC CAGGGGACAT CTCAGGCTTG CAGGGTGGCC
1150 CCCGCTCCGA CTTCGACATG GCCTATGAGC GTGGCCGGAT CTCCGTGTCC
1200 CTGCAAGAAG AGGCCTCCGG GGGGTCCCTG GCAGCCCCCG CTCGGACCCC
1250 CACTCAGGAG CCTCGTGAGC AGCCGGCAGG CGCCTGTGAA TACAGCTACT
1300 GTGAGGATGA GTCGGCCACT GGTGGCTGCC CTTTCGGGCC CTACCAGGGC
1350 CGCCAGACCA GCAGCATCTT CGAGGCAGCA AAGCAGGAGC TGGCCAAGCT
1400 GATGCGGATT GAGGACCCCT CCCTCCTGAA CAGCAGAGTC TTGCTGCACC
1450 ACGCAAAGC TGGCACCATC ATTGCCCGCC AGGGAGACCA GGACGTGAGC
1500 CTGCACTTCG TGCTCTGGGG CTGCCTGCAC GTGTACCAGC GCATGATCGA
1550 CAAGGCGGAG GACGTGTGCC TGTTCGTAGC GCAGCCCGGG GAACTGGTGG
1600 GGCAGCTGGC GGTGCTCACT GGCGAACCTC TCATCTTCAC ACTGCGAGCC
1650 CAACGCGACT GCACCTTCCT GCGGATCTCC AAGTCCGACT TCTATGAGAT
1700 CATGCGCGCA CAGCCCAGTG TGGTGCTGAG TGCGGCGCAC ACGGTGGCAG
1750 CCAGGATGTC GCCCTTCGTG CGCCAGATGG ACTTCGCCAT CGACTGGACT
1800 GCAGTGGAGG CGGGACGCGC GCTGTACAGG CAGGGCGACC GCTCCGACTG
1850 CACTTACATC GTGCTCAATG GCGGCTGCG TAGCGTGATC CAGCGAGGCA
1900 GTGGCAAGAA GGAGCTGGTG GGCGAGTACG CCGCGGCGA CCTCATCGGC
1950 GTGGTGGAGG CACTGACCCG GCAGCCGCGA GCCACGACGG TGCACGCGGT
2000 GCGCGACACG GAGCTGGCCA AGCTTCCCGA GGGCACCTTG GGTCACATCA
2050 AACGCCGGTA CCCGCAGGTC GTGACCCGCC TTATCCACCT ACTGAGCCAG
2100 AAAATTCTAG GAATTTGCA GCAGCTGCAA GGACCCTTCC CAGCAGGCTC
2150 TGGGTTGGGT GTGCCCCCAC ACTCGGAACT CACCAACCCA GCCAGCAACC
2200 TGGCAACTGT GGCAATCCTG CCTGTGTGTG CTGAGGTCCC CATGGTGGCC
2250 TTCACGCTGG AGCTGCAGCA CGCCCTGCAG GCCATCGGTC CGACGCTACT
2300 CCTTAACAGT GACATCATCC GGGCACGCCT GGGGGCCTCC GCACTGGATA
2350 GCATCCAAGA GTTCCGGCTG TCAGGGTGGC TGGCCCAGCA GGAGGATGCA
2400 CACCGTATCG TACTCTACCA GACGGACGCC TCGCTGACGC CCTGGACCGT
2450 GCGCTGCCTG CGACAGGCCG ACTGCATCCT CATTGTGGGC CTGGGGGACC
```

FIGURE 2 - B

```
2500 AGGAGCCTAC CCTCGGCCAG CTGGAGCAGA TGCTGGAGAA CACGGCTGTG
2550 CGCGCCCTTA AGCAGCTAGT CCTGCTCCAC CGAGAGGAGG GCGCGGGCCC
2600 CACGCGCACC GTGGAGTGGC TAAATATGCG CAGCTGGTGC TCGGGGCACC
2650 TGCACCTGCG CTGTCCGCGC CGCCTCTTTT CGCGCCGCAG CCCTGCCAAG
2700 CTGCATGAGC TCTACGAGAA GGTTTTCTCC AGGCGCGCGG ACCGGCACAG
2750 CGACTTCTCC CGCTTGGCGA GGGTGCTCAC GGGGAACACC ATTGCCCTTG
2800 TGCTAGGCGG GGGCGGGGCC AGGGGCTGCT CGCACATCGG AGTACTAAAG
2850 GCATTAGAGG AGGCGGGGGT CCCCGTGGAC CTGGTGGGCG GCACGTCCAT
2900 TGGCTCTTTC ATCGGAGCGT TGTACGCGGA GGAGCGCAGC GCCAGCCGCA
2950 CGAGGCAGCG GGCCCGGGAG TGGGCCAAGA GCATGACTTC GGTGCTGGAA
3000 CCTGTGTTGG ACCTCACGTA CCCAGTCACC TCCGTGTTCA CTGGGTCTGC
3050 CTTTAACCGC AGCATCCATC GGGTCTTCCA GGATAAGCAG ATTGAGGACC
3100 TGTGGCTGCC TTACTTCAAC GTGACCACAG ATATCACCGC CTCAGCCATG
3150 CGAGTCCACA AAGATGGCTC CCTGTGGCGG TACGTGCGCG CCAGCATGAC
3200 GCTGTCGGGC TACCTGCCCC CGCTGTGCGA CCCCAAGGAC GGGCACCTAC
3250 TCATGGATGG CGGCTACATC AACAATCTGC CAGCGGACAT CGCCCGCAGC
3300 ATGGGTGCCA AAACGGTCAT CGCCATTGAC GTGGGGAGCC AGGATGAGAC
3350 GGACCTCAGC ACCTACGGGG ACAGCCTGTC CGGCTGGTGG CTGCTGTGGA
3400 AGCGGCTGAA TCCCTGGGCT GACAAGGTAA AGGTTCCAGA CATGGCTGAA
3450 ATCCAGTCCC GCCTGGCCTA CGTGTCCTGT GTGCGGCAGC TAGAGGTTGT
3500 CAAGTCCAGC TCCTACTGCG AGTACCTGCG CCCGCCCATC GACTGCTTCA
3550 AGACCATGGA CTTTGGGAAG TTCGACCAGA TCTATGATGT GGGCTACCAG
3600 TACGGGAAGG CGGTGTTTGG AGGCTGGAGC CGTGGCAACG TCATTGAGAA
3650 AATGCTCACA GACCGGCGGT CTACAGACCT TAATGAGAGC CGCCGTGCAG
3700 ACGTGCTTGC CTTCCCAAGC TCTGGCTTCA CTGACTTGGC AGAGATTGTG
3750 TCCCGGATTG AGCCCCCCAC GAGCTATGTC TCTGATGGCT GTGCTGACGG
3800 AGAGGAGTCA GATTGTCTGA CAGAGTATGA GGAGGACGCC GGACCCGACT
3850 GCTCGAGGGA TGAAGGGGGG TCCCCGAGG GCGCAAGCCC CAGCACTGCC
3900 TCCGAGATGG AGGAGGAGAA GTCGATTCTC CGGCAACGAC GCTGTCTGCC
3950 CCAGGAGCCG CCCGGCTCAG CCACAGATGC CTGAGGACCT CGACAGGGGT
4000 CACCCCCTCC CTCCCACCCC TGGACTGGGC TGGGGGTGGC CCCGTGGGGG
4050 TAGCTCACTC CCCCTCCTGC TGCTATGCCT GTGACCCCCG CGGCCCACAC
4100 ACTGGACTGA CCTGCCCTGA GCGGGGATGC AGTGTTGCAC TGATGACTTG
4150 ACCAGCCCCT CCCCCAATAA ACTCGCCTCT TGGAAAAAAA AAAAAAAAA
4200 AAAAAAAAAA AAAAAAAAA AAAAA
```

FIGURE 3 - A
SEQ ID NO: 3

```
                              10                    20
30                    40                    50
   0 ATGGAGGCTC CGCTGCAAAC TGGAATGGTG CTTGGCGTGA TGATCGGGGC
  50 CGGAGTGGCG GTGGTGGTCA CGGCCGTGCT CATCCTCCTG GTGGTGCGGA
 100 GGCTGCGAGT GCCAAAAACC CCAGCCCCGG ATGGCCCCCG GTATCGGTTC
 150 CGGAAGAGGG ACAAAGTGCT CTTCTATGGC CGGAAGATTA TGCGGAAGGT
 200 GTCACAATCC ACCTCCTCCC TCGTGGATAC CTCTGTCTCC GCCACCTCCC
 250 GGCCACGCAT GAGGAAGAAA CTGAAGATGC TCAACATTGC CAAGAAGATC
 300 CTGCGCATCC AGAAAGAGAC GCCCACGCTG CAGCGGAAGG AGCCCCCGCC
 350 CGCAGTGCTA GAAGCTGACC TGACCGAGGG CGACCTGGCT AACTCCCATC
 400 TGCCCTCTGA AGTGCTTTAT ATGCTCAAGA ACGTCCGGGT GCTGGGCCAC
 450 TTCGAGAAGC CACTCTTCCT GGAGCTCTGC CGCCACATGG TCTTCCAGCG
 500 GCTGGGCCAG GGTGACTACG TCTTCCGGCC GGGCCAGCCA GATGCCAGCA
 550 TCTACGTGGT GCAGGACGGG CTGCTGGAGC TCTGTCTGCC AGGGCCTGAC
 600 GGGAAGGAGT GTGTGGTGAA GGAAGTGGTT CCTGGGGACA GCGTCAACAG
 650 CCTTCTCAGC ATCCTGGATG TCATCACCGG TCACCAGCAT CCCCAGCGGA
 700 CCGTGTCTGC CCGGGCGGCC CGGGACTCCA CGGTGCTGCG CCTGCCGGTG
 750 GAAGCATTCT CCGCGGTCTT CACCAAGTAC CCGGAGAGCT TGGTGCGGGT
 800 CGTGCAGATC ATCATGGTGC GGCTGCAGCG AGTCACCTTC CTGGCACTGC
 850 ACAACTACCT GGGTCTGACC AATGAGCTCT TCAGCCACGA GATCCAGCCC
 900 CTGCGTCTGT TCCCCAGCCC CGGCCTCCCA ACTCGCACCA GCCCTGTGCG
 950 GGGCTCCAAG AGAATGGTCA GCACCTCAGC TACAGACGAG CCCAGGGAGA
1000 CCCCAGGGCG GCCACCCGAT CCCACCGGGG CCCCGCTGCC TGGACCTACA
1050 GGGGACCCTG TGAAGCCCAC ATCCCTGGAA ACCCCCTCGC CCCCTCTGCT
1100 GAGCCGCTGC GTCTCCATGC CAGGGGACAT CTCAGGCTTG CAGGGTGGCC
1150 CCCGCTCCGA CTTCGACATG GCCTATGAGC GTGGCCGGAT CTCCGTGTCC
1200 CTGCAAGAAG AGGCCTCCGG GGGGTCCCTG GCAGCCCCCG CTCGGACCCC
1250 CACTCAGGAG CCTCGTGAGC AGCCGGCAGG CGCCTGTGAA TACAGCTACT
1300 GTGAGGATGA GTCGGCCACT GGTGGCTGCC CTTTCGGGCC CTACCAGGGC
1350 CGCCAGACCA GCAGCATCTT CGAGGCAGCA AAGCAGGAGC TGGCCAAGCT
1400 GATGCGGATT GAGGACCCCT CCCTCCTGAA CAGCAGAGTC TTGCTGCACC
1450 ACGCCAAAGC TGGCACCATC ATTGCCCGCC AGGGAGACCA GGACGTGAGC
1500 CTGCACTTCG TGCTCTGGGG CTGCCTGCAC GTGTACCAGC GCATGATCGA
1550 CAAGGCGGAG GACGTGTGCC TGTTCGTAGC GCAGCCCGGG GAACTGGTGG
1600 GGCAGCTGGC GGTGCTCACT GGCGAACCTC TCATCTTCAC ACTGCGAGCC
1650 CAACGCGACT GCACCTTCCT GCGGATCTCC AAGTCCGACT TCTATGAGAT
1700 CATGCGCGCA CAGCCCAGTG TGGTGCTGAG TGCGGCGCAC ACGGTGGCAG
1750 CCAGGATGTC GCCCTTCGTG CGCCAGATGG ACTTCGCCAT CGACTGGACT
1800 GCAGTGGAGG CGGGACGCGC GCTGTACAGG CAGGGCGACC GCTCCGACTG
1850 CACTTACATC GTGCTCAATG GCGGCTGCG TAGCGTGATC CAGCGAGGCA
1900 GTGGCAAGAA GGAGCTGGTG GGCGAGTACG CCGCGGCGA CCTCATCGGC
1950 GTGGTGGAGG CACTGACCCG GCAGCCGCGA GCCACGACGG TGCACGCGGT
2000 GCGCGACACG GAGCTGGCCA AGCTTCCCGA GGGCACCTTG GGTCACATCA
2050 AACGCCGGTA CCCGCAGGTC GTGACCCGCC TTATCCACCT ACTGAGCCAG
2100 AAAATTCTAG GGAATTTGCA GCAGCTGCAA GGACCCTTCC AGCAGGCTC
2150 TGGGTTGGGT GTGCCCCCAC ACTCGGAACT CACCAACCCA GCCAGCAACC
2200 TGGCAACTGT GGCAATCCTG CCTGTGTGTG CTGAGGTCCC CATGGTGGCC
2250 TTCACGCTGG AGCTGCAGCA CGCCCTGCAG GCCATCGGTC GACGCTACT
2300 CCTTAACAGT GACATCATCC GGGCACGCCT GGGGGCCTCC GCACTGGATA
2350 GCATCCAAGA GTTCCGGCTG TCAGGGTGGC TGGCCCAGTA GGAGGATGCA
2400 CACCGTATCG TACTCTACCA GACGGACGCC TCGCTGACGC CCTGGACCGT
2450 GCGCTGCCTG CGACAGGCCG ACTGCATCCT CATTGTGGGC CTGGGGGACC
```

FIGURE 3 - B

```
2500 AGGAGCCTAC CCTCGGCCAG CTGGAGCAGA TGCTGGAGAA CACGGCTGTG
2550 CGCGCCCTTA AGCAGCTAGT CCTGCTCCAC CGAGAGGAGG GCGCGGGCCC
2700 CTGCATGAGC TCTACGAGAA GGTTTTCTCC AGGCGCGCGG ACCGGCACAG
2600 CACGCGCACC GTGGAGTGGC TAAATATGCG CAGCTGGTGC TCGGGCACC
2650 TGCACCTGCG CTGTCCGCGC CGCCTCTTTT CGCGCCGCAG CCCTGCCAAG
2700 CTGCATGAGC TCTACGAGAA GGTTTTCTCC AGGCGCGCGG ACCGGCACAG
2750 CGACTTCTCC CGCTTGGCGA GGGTGCTCAC GGGGAACACC ATTGCCCTTG
2800 TGCTAGGCGG GGGCGGGGCC AGGGGCTGCT CGCACATCGG AGTACTAAAG
2850 GCATTAGAGG AGGCGGGGGT CCCCGTGGAC CTGGTGGGCG GCACGTCCAT
2900 TGGCTCTTTC ATCGGAGCGT TGTACGCGGA GGAGCGCAGC GCCAGCCAGCCGCA
2950 CGAGGCAGCG GGCCCGGGAG TGGGCCAAGA GCATGACTTC GGTGCTGGAA
3000 CCTGTGTTGG ACCTCACGTA CCCAGTCACC TCCATGTTCA CTGGGTCTGC
3050 CTTTAACCGC AGCATCCATC GGGTCTTCCA GGATAAGCAG ATTGAGGACC
3100 TGTGGCTGCC TTACTTCAAC GTGACCACAG ATATCACCGC CTCAGCCATG
3150 CGAGTCCACA AAGATGGCTC CCTGTGGCGG TACGTGCGCG CCAGCATGAC
3200 GCTGTCGGGC TACCTGCCCC CGCTGTGCGA CCCCAAGGAC GGGCACCTAC
3250 TCATGGATGG CGGCTACATC AACAATCTGC CAGCGGACAT CGCCCGCAGC
3300 ATGGGTGCCA AAACGGTCAT CGCCATTGAC GTGGGGAGCC AGGATGAGAC
3350 GGACCTCAGC ACCTACGGGG ACAGCCTGTC CGGCTGGTGG CTGCTGTGGA
3400 AGCGGCTGAA TCCCTGGGCT GACAAGGTAA AGGTTCCAGA CATGGCTGAA
3450 ATCCAGTCCC GCCTGGCCTA CGTGTCCTGT GTGCGGCAGC TAGAGGTTGT
3500 CAAGTCCAGC TCCTACTGCG AGTACCTGCG CCCGCCCATC GACTGCTTCA
3550 AGACCATGGA CTTTGGGAAG TTCGACCAGA TCTATGATGT GGGCTACCAG
3600 TACGGGAAGG CGGTGTTTGG AGGCTGGAGC CGTGGCAACG TCATTGAGAA
3650 AATGCTCACA GACCGGCGGT CTACAGACCT TAATGAGAGC CGCCGTGCAG
3700 ACGTGCTTGC CTTCCCAAGC TCTGGCTTCA CTGACTTGGC AGAGATTGT
3750 TCCCGGATTG AGCCCCCCAC GAGCTATGTC TCTGATGGCT GTGCTGACGG
3800 AGAGGAGTCA GATTGTCTGA CAGAGTATGA GGAGGACGCC GGACCCGACT
3850 GCTCGAGGGA TGAAGGGGGG TCCCCGAGG GCGCAAGCCC CAGCACTGCC
3900 TCCGAGATGG AGGAGGAGAA GTCGATTCTC CGGCAACGAC GCTGTCTGCC
3950 CCAGGAGCCG CCCGGCTCAG CCACAGATGC CTGAGGACCT CGACAGGGGT
4000 CACCCCCTCC CTCCCACCCC TGGACTGGGC TGGGGGTGGC CCCGTGGGGG
4050 TAGCTCACTC CCCCTCCTGC TGCTATGCCT GTGACCCCCG CGGCCCACAC
4100 ACTGGACTGA CCTGCCCTGA GCGGGGATGC AGTGTTGCAC TGATGACTTG
4150 ACCAGCCCCT CCCCCAATAA ACTCGCCTCT TGGAAAAAAA AAAAAAAAA
4200 AAAAAAAAAA AAAAAAAAA AAAAA
```

FIGURE 4 - A
SEQ ID NO: 4

```
                                 10                            20
30                       40                    50
   0 ATGGAGGCTC CGCTGCAAAC TGGAATGGTG CTTGGCGTGA TGATCGGGGC
  50 CGGAGTGGCG GTGGTGGTCA CGGCCGTGCT CATCCTCCTG GTGGTGCGGA
 100 GGCTGCGAGT GCCAAAAACC CCAGCCCCGG ATGGCCCCCG GTATCGGTTC
 150 CGGAAGAGGG ACAAAGTGCT CTTCTATGGC CGGAAGATTA TGCGGAAGGT
 200 GTCACAATCC ACCTCCTCCC TCGTGGATAC CTCTGTCTCC GCCACCTCCC
 250 GGCCACGCAT GAGGAAGAAA CTGAAGATGC TCAACATTGC CAAGAAGATC
 300 CTGCGCATCC AGAAAGAGAC GCCCACGCTG CAGCGGAAGG AGCCCCCGCC
 350 CGCAGTGCTA GAAGCTGACC TGACCGAGGG CGACCTGGCT AACTCCCATC
 400 TGCCCTCTGA AGTGCTTTAT ATGCTCAAGA ACGTCCGGGT GCTGGGCCAC
 450 TTCGAGAAGC CACTCTTCCT GGAGCTCTGC CGCCACATGG TCTTCCAGCG
 500 GCTGGGCCAG GGTGACTACG TCTTCCGGCC GGGCCAGCCA GATGCCAGCA
 550 TCTACGTGGT GCAGGACGGG CTGCTGGAGC TCTGTCTGCC AGGGCCTGAC
 600 GGGAAGGAGT GTGTGGTGAA GGAAGTGGTT CCTGGGGACA GCGTCAACAG
 650 CCTTCTCAGC ATCCTGGATG TCATCACCGG TCACCAGCAT CCCCAGCGGA
 700 CCGTGTCTGC CCGGGCGGCC CGGGACTCCA CGGTGCTGCG CCTGCCGGTG
 750 GAAGCATTCT CCGCGGTCTT CACCAAGTAC CCGGAGAGCT TGGTGCGGGT
 800 CGTGCAGATC ATCATGGTGC GGCTGCAGCG AGTCACCTTC CTGGCACTGC
 850 ACAACTACCT GGGTCTGACC AATGAGCTCT CAGCCACGA GATCCAGCCC
 900 CTGCGTCTGT TCCCCAGCCC CGGCCTCCCA ACTCGCACCA GCCCTGTGCG
 950 GGGCTCCAAG AGAATGGTCA GCACCTCAGC TACAGACGAG CCCAGGGAGA
1000 CCCCAGGGCG GCCACCCGAT CCCACCGGGG CCCCGCTGCC TGGACCTACA
1050 GGGGACCCTG TGAAGCCCAC ATCCCTGGAA ACCCCCTCGC CCCCTCTGCT
1100 GAGCCGCTGC GTCTCCATGC CAGGGGACAT CTCAGGCTTG CAGGGTGGCC
1150 CCCGCTCCGA CTTCGACATG GCCTATGAGC GTGGCCGGAT CTCCGTGTCC
1200 CTGCAAGAAG AGGCCTCCGG GGGGTCCCTG GCAGCCCCG CTCGGACCCC
1250 CACTCAGGAG CCTCGTGAGC AGCCGGCAGG CGCCTGTGAA TACAGCTACT
1300 GTGAGGATGA GTCGGCCACT GGTGGCTGCC CTTTCGGGCC CTACCAGGGC
1350 CGCCAGACCA GCAGCATCTT CGAGGCAGCA AAGCAGGAGC TGGCCAAGCT
1400 GATGCGGATT GAGGACCCCT CCCTCCTGAA CAGCAGAGTC TTGCTGCACC
1450 ACGCCAAAGC TGGCACCATC ATTGCCCGCC AGGGAGACCA GGACGTGAGC
1500 CTGCACTTCG TGCTCTGGGG CTGCCTGCAC GTGTACCAGC GCATGATCGA
1550 CAAGGCGGAG GACGTGTGCC TGTTCGTAGC GCAGCCCGGG GAACTGGTGG
1600 GGCAGCTGGC GGTGCTCACT GGCGAACCTC TCATCTTCAC ACTGCAGCC
1650 CAACGCGACT GCACCTTCCT GCGGATCTCC AAGTCCGACT TCTATGAGAT
1700 CATGCGCGCA CAGCCCAGTG TGGTGCTGAG TGCGGCGCAC ACGGTGGCAG
1750 CCAGGATGTC GCCCTTCGTG CGCCAGATGG ACTTCGCCAT CGACTGGACT
1800 GCAGTGGAGG CGGGACGCGC GCTGTACAGG CAGGGCGACC GCTCCGACTG
1850 CACTTACATC GTGCTCAATG GCGGCTGCG TAGCGTGATC CAGCGAGGCA
1900 GTGGCAAGAA GGAGCTGGTG GCGAGTACG GCCGCGGCGA CCTCATCGGC
1950 GTGGTGGAGG CACTGACCCG GCAGCCGCGA GCCACGACGG TGCACGCGGT
2000 GCGCGACACG GAGCTGGCCA AGCTTCCCGA GGGCACCTTG GGTCACATCA
2050 AACGCCGGTA CCCGCAGGTC GTGACCCGCC TTATCCACCT ACTGAGCCAG
2100 AAAATTCTAG GAATTTGCA GCAGCTGCAA GGACCTTCC CAGCAGGCTC
2150 TGGGTTGGGT GTGCCCCAC ACTCGGAACT CACCAACCCA GCCAGCAACC
2200 TGGCAACTGT GGCAATCCTG CCTGTGTGTG CTGAGGTCCC CATGGTGGCC
2250 TTCACGCTGG AGCTGCAGCA CGCCCTGCAG GCCATCGGTC CGACGCTACT
2300 CCTTAACAGT GACATCATCC GGGCACGCCT GGGGGCCTCC GCACTGGATA
2350 GCATCCAAGA GTTCCGGCTG TCAGGGTGGC TGGCCCAGCA GGAGGATGCA
2400 CACCGTATCG TACTCTACCA GACGGACGCC TCGCTGACGC CCTGGACCGT
2450 GCGCTGCCTG CGACAGGCCG ACTGCATCCT CATTGTGGGC CTGGGGGACC
```

FIGURE 4 - B

```
2500 AGGAGCCTAC CCTCGGCCAG CTGGAGCAGA TGCTGGAGAA CACGGCTGTG
2550 CGCGCCCTTA AGCAGCTAGT CCTGCTCCAC CGAGAGGAGG GCGCGGGCCC
2600 CACGCGCACC GTGGAGTGGC TAAATATGCG CAGCTGGTGC TCGGGGCACC
2650 TGCACCTGCG CTGTCCGCGC CGCCTCTTTT CGCGCCGCAG CCCTGCCAAG
2700 CTGCATGAGC TCTACGAGAA GGTTTTCTCC AGGCGCGCGG ACCGGCACAG
2750 CGACTTCTCC CGCTTGGCGA GGGTGCTCAC GGGGAACACC ATTGCCCTTG
2800 TGCTAGGCGG GGGCGGGGCC AGGGGCTGCT CGCACATCGG AGTACTAAAG
2850 GCATTAGAGG AGGCGGGGGT CCCCGTGGAC CTGGTGGGCG GCACGTCCAT
2900 TGGCTCTTTC ATCGGAGCGT TGTACGCGGA GGAGCGCAGC GCCAGCCGCA
2950 CGGGGCAGCG GGCCCGGGAG TGGGCCAAGA GCATGACTTC GGTGCTGGAA
3000 CCTGTGTTGG ACCTCACGTA CCCAGTCACC TCCATGTTCA CTGGGTCTGC
3050 CTTTAACCGC AGCATCCATC GGGTCTTCCA GGATAAGCAG ATTGAGGACC
3100 TGTGGCTGCC TTACTTCAAC GTGACCACAG ATATCACCGC CTCAGCCATG
3150 CGAGTCCACA AAGATGGCTC CCTGTGGCGG TACGTGCGCG CCAGCATGAC
3200 GCTGTCGGGC TACCTGCCCC CGCTGTGCGA CCCCAAGGAC GGGCACCTAC
3250 TCATGGATGG CGGCTACATC AACAATCTGC CAGCGGACAT CGCCCGCAGC
3300 ATGGGTGCCA AAACGGTCAT CGCCATTGAC GTGGGGAGCC AGGATGAGAC
3350 GGACCTCAGC ACCTACGGGG ACAGCCTGTC CGGCTGGTGG CTGCTGTGGA
3400 AGCGGCTGAA TCCCTGGGCT GACAAGGTAA AGGTTCCAGA CATGGCTGAA
3450 ATCCAGTCCC GCCTGGCCTA CGTGTCCTGT GTGCGGCAGC TAGAGGTTGT
3500 CAAGTCCAGC TCCTACTGCG AGTACCTGCG CCCGCCCATC GACTGCTTCA
3550 AGACCATGGA CTTTGGGAAG TTCGACCAGA TCTATGATGT GGGCTACCAG
3600 TACGGGAAGG CGGTGTTTGG AGGCTGGAGC CGTGGCAACG TCATTGAGAA
3650 AATGCTCACA GACCGGCGGT CTACAGACCT TAATGAGAGC CGCCGTGCAG
3700 ACGTGCTTGC CTTCCAAGC TCTGGCTTCA CTGACTTGGC AGAGATTGTG
3750 TCCCGGATTG AGCCCCCCAC GAGCTATGTC TCTGATGGCT GTGCTGACGG
3800 AGAGGAGTCA GATTGTCTGA CAGAGTATGA GGAGGACGCC GGACCCGACT
3850 GCTCGAGGGA TGAAGGGGGG TCCCCCGAGG GCGCAAGCCC CAGCACTGCC
3900 TCCGAGATGG AGGAGGAGAA GTCGATTCTC CGGCAACGAC GCTGTCTGCC
3950 CCAGGAGCCG CCCGGCTCAG CCACAGATGC CTGAGGACCT CGACAGGGGT
4000 CACCCCCTCC CTCCCACCCC TGGACTGGGC TGGGGTGGC CCCGTGGGGG
4050 TAGCTCACTC CCCCTCCTGC TGCTATGCCT GTGACCCCCG CGGCCCACAC
4100 ACTGGACTGA CCTGCCCTGA GCGGGATGC AGTGTTGCAC TGATGACTTG
4150 ACCAGCCCCT CCCCCAATAA ACTCGCCTCT TGGAAAAAAA AAAAAAAAA
4200 AAAAAAAAAA AAAAAAAAAA AAAAA
```

FIGURE 5

SEQ ID NO: 5

```
   0 MEAPLQTGMV LGVMIGAGVA VVVTAVLILL VVRRLRVPKT PAPDGPRYRF
  50 RKRDKVLFYG RKIMRKVSQS TSSLVDTSVS ATSRPRMRKK LKMLNIAKKI
 100 LRIQKETPTL QRKEPPPAVL EADLTEGDLA NSHLPSEVLY MLKNVRVLGH
 150 FEKPLFLELC RHMVFQRLGQ GDYVFRPGQP DASIYVVQDG LLELCLPGPD
 200 GKECVVKEVV PGDSVNSLLS ILDVITGHQH PQRTVSARAA RDSTVLRLPV
 250 EAFSAVFTKY PESLVRVVQI IMVRLQRVTF LALHNYLGLT NELFSHEIQP
 300 LRLFPSPGLP TRTSPVRGSK RMVSTSATDE PRETPGRPPD PTGAPLPGPT
 350 GDPVKPTSLE TPSPPLLSRC VSMPGDISGL QGGPRSDFDM AYERGRISVS
 400 LQEEASGGSL AAPARTPTQE PREQPAGACE YSYCEDESAT GGCPFGPYQG
 450 RQTSSIFEAA KQELAKLMRI EDPSLLNSRV LLHHAKAGTI IARQGDQDVS
 500 LHFVLWGCLH VYQRMIDKAE DVCLFVAQPG ELVGQLAVLT GEPLIFTLRA
 550 QRDCTFLRIS KSDFYEIMRA QPSVVLSAAH TVAARMSPFV RQMDFAIDWT
 600 AVEAGRALYR QGDRSDCTYI VLNGRLRSVI QRGSGKKELV GEYGRGDLIG
 650 VVEALTRQPR ATTVHAVRDT ELAKLPEGTL GHIKRRYPQV VTRLIHLLSQ
 700 KILGNLQQLQ GPFPAGSGLG VPPHSELTNP ASNLATVAIL PVCAEVPMVA
 750 FTLELQHALQ AIGPTLLLNS DIIRARLGAS ALDSIQEFRL SGWLAQQEDA
 800 HRIVLYQTDA SLTPWTVRCL RQADCILIVG LGDQEPTLGQ LEQMLENTAV
 850 RALKQLVLLH REEGAGPTRT VEWLNMRSWC SGHLHLRCPR RLFSRRSPAK
 900 LHELYEKVFS RRADRHSDFS RLARVLTGNT IALVLGGGGA RGCSHIGVLK
 950 ALEEAGVPVD LVGGTSIGSF IGALYAEERS ASRTQRARE WAKSMTSVLE
1000 PVLDLTYPVT SMFTGSAFNR SIHRVFQDKQ IEDLWLPYFN VTTDITASAM
1050 RVHKDGSLWR YVRASMTLSG YLPPLCDPKD GHLLMDGGYI NNLPADIARS
1100 MGAKTVIAID VGSQDETDLS TYGDSLSGWW LLWKRLNPWA DKVKVPDMAE
1150 IQSRLAYVSC VRQLEVVKSS SYCEYLRPPI DCFKTMDFGK FDQIYDVGYQ
1200 YGKAVFGGWS RGNVIEKMLT DRRSTDLNES RRADVLAFPS SGFTDLAEIV
1250 SRIEPPTSYV SDGCADGEES DCLTEYEEDA GPDCSRDEGG SPEGASPSTA
1300 SEMEEEKSIL RQRRCLPQEP PGSATDA!GP RQGSPPPSHP WTGLGVAPWG
1350 !LTPPPAAMP VTPAAHTLD! PALSGDAVLH !!LDQPLPQ! TRLLEKKKKK
1400 KKKKKKKK
```

FIGURE 6

SEQ ID NO: 6

```
   0 MEAPLQTGMV LGVMIGAGVA VVVTAVLILL VVRRLRVPKT PAPDGPRYRF
  50 RKRDKVLFYG RKIMRKVSQS TSSLVDTSVS ATSRPRMRKK LKMLNIAKKI
 100 LRIQKETPTL QRKEPPPAVL EADLTEGDLA NSHLPSEVLY MLKNVRVLGH
 150 FEKPLFLELC RHMVFQRLGQ GDYVFRPGQP DASIYVVQDG LLELCLPGPD
 200 GKECVVKEVV PGDSVNSLLS ILDVITGHQH PQRTVSARAA RDSTVLRLPV
 250 EAFSAVFTKY PESLVRVVQI IMVRLQRVTF LALHNYLGLT NELFSHEIQP
 300 LRLFPSPGLP TRTSPVRGSK RMVSTSATDE PRETPGRPPD PTGAPLPGPT
 350 GDPVKPTSLE TPSPPLLSRC VSMPGDISGL QGGPRSDFDM AYERGRISVS
 400 LQEEASGGSL AAPARTPTQE PREQPAGACE YSYCEDESAT GGCPFGPYQG
 450 RQTSSIFEAA KQELAKLMRI EDPSLLNSRV LLHHAKAGTI IARQGDQDVS
 500 LHFVLWGCLH VYQRMIDKAE DVCLFVAQPG ELVGQLAVLT GEPLIFTLRA
 550 QRDCTFLRIS KSDFYEIMRA QPSVVLSAAH TVAARMSPFV RQMDFAIDWT
 600 AVEAGRALYR QGDRSDCTYI VLNGRLRSVI QRGSGKKELV GEYGRGDLIG
 650 VVEALTRQPR ATTVHAVRDT ELAKLPEGTL GHIKRRYPQV VTRLIHLLSQ
 700 KILGNLQQLQ GPFPAGSGLG VPPHSELTNP ASNLATVAIL PVCAEVPMVA
 750 FTLELQHALQ AIGPTLLLNS DIIRARLGAS ALDSIQEFRL SGWLAQQEDA
 800 HRIVLYQTDA SLTPWTVRCL RQADCILIVG LGDQEPTLGQ LEQMLENTAV
 850 RALKQLVLLH REEGAGPTRT VEWLNMRSWC SGHLHLRCPR RLFSRRSPAK
 900 LHELYEKVFS RRADRHSDFS RLARVLTGNT IALVLGGGGA RGCSHIGVLK
 950 ALEEAGVPVD LVGGTSIGSF IGALYAEERS ASRTRQRARE WAKSMTSVLE
1000 PVLDLTYPVT SVFTGSAFNR SIHRVFQDKQ IEDLWLPYFN VTTDITASAM
1050 RVHKDGSLWR YVRASMTLSG YLPPLCDPKD GHLLMDGGYI NNLPADIARS
1100 MGAKTVIAID VGSQDETDLS TYGDSLSGWW LLWKRLNPWA DKVKVPDMAE
1150 IQSRLAYVSC VRQLEVVKSS SYCEYLRPPI DCFKTMDFGK FDQIYDVGYQ
1200 YGKAVFGGWS RGNVIEKMLT DRRSTDLNES RRADVLAFPS SGFTDLAEIV
1250 SRIEPPTSYV SDGCADGEES DCLTEYEEDA GPDCSRDEGG SPEGASPSTA
1300 SEMEEEKSIL RQRRCLPQEP PGSATDA!GP RQGSPPPSHP WTGLGVAPWG
1350 !LTPPPAAMP VTPAAHTLD! PALSGDAVLH !!LDQPLPQ! TRLLEKKKKK
1400 KKKKKKKK
```

COMPOSITIONS AND METHODS FOR DETECTING AND TREATING MOTOR NEURON DISORDERS

This Application claims priority to provisional patent application Ser. No. 60/635,459, filed Dec. 13, 2004, which is herein incorporated by reference in its entirety.

This invention was made with government support under Grants Nos. NS33645 and NS045163 awarded by the National Institutes of Health.

FIELD OF THE INVENTION

The present invention relates to the NTE proteins and nucleic acids encoding the NTE proteins. The present invention further provides assays for the detection of NTE polymorphisms and mutations associated with disease states, as well as methods of screening for therapeutic agents, ligands, and modulators of NTE proteins.

BACKGROUND OF THE INVENTION

Motor neuron disorders include amyotrophic lateral sclerosis, autosomal recessive spastic paraplegia, hereditary spastic paraplegia, primary lateral sclerosis, progressive pseudobulbar palsy, progressive muscular atrophy, progressive bulbar palsy, and postpolio syndrome. Symptoms characteristic for a specific type of motor neuron disorder vary according to the part of the nervous system most affected. Median age of onset for developing a motor neuron disorder is 55 years, with a higher incidence in males. 5% of motor neuron cases are familial with autosomal dominant inheritance.

Clinical aspects of motor neuron disorders involve debilitating symptoms resulting commonly in death. Amyotrophic lateral sclerosis, for example, involves muscular weakness, atrophy and signs of anterior horn cell dysfunction. The site of onset is random, and progression is asymmetric. Cramps are common and may precede weakness. Visible muscle twitches (fasciculations), spasticity, hyperactive deep tendon reflexes, extensor plantar reflexes, and signs of corticospinal tract involvement soon follow. Dysarthria and dysphagia are due to involvement of brain stem nuclei and pathways. Sensory systems, voluntary eye movements, and urinary sphincters are spared. Rarely, a patient survives 30 years, while 50% die within three years of onset, 20% live for 5 years, and 10% live 10 years.

Autosomal hereditary spastic paraplegia, for example, involves an age of onset varying from childhood to old age. Pathologic findings include degeneration of the descending corticospinal tracts and fasciculus gracilis, despite the absence of sensory findings. Anterior horn cell dropout has been reported. The disorder may occur with other neurologic abnormalities, including spinocerebellar and ocular symptoms (Ferguson-Critchley syndrome), extrapyramidal symptoms, optic atrophy, retinal degeneration (Kjellin syndrome), mental retardation or dementia, and polyneuropathy. The etiology of these syndromes is unknown. Symptoms and signs include progressive gait difficulties, hyperreflexia, clonus, and Babinski's sign. Sensory and sphincteric functions are usually spared. Arms may also be affected.

Motor neuron disorder diagnostic features include onset during middle or late adult life and progressive, generalized motor involvement without sensory abnormalities. Nerve conduction velocities are normal until late in the disease. Electromyography is the most useful test, showing fibrillations, positive waves, fasciculations, and giant motor units, even in unaffected limbs.

There is no specific treatment for motor neuron disorders. Physical therapy may help maintain muscle function. Patients with pharyngeal weakness are fed with extreme care and require a gastrostomy. Baclofen is used to reduce spasticity. Quinine or phenytoin is used to decrease cramps. A strongly anticholinergic drug, such as amitriptyline, is used to decrease saliva production. Surgery to improve swallowing has limited success in patients with progressive bulbar palsy.

Improved therapies aimed at decreasing motor neuron disorder symptoms are needed. Preventive strategies aimed at preventing the onset of motor neuron disorders are also needed. In addition, improved methods of identifying individuals at risk for developing motor neuron disorders are needed.

SUMMARY OF THE INVENTION

The present invention relates to the NTE proteins and nucleic acids encoding the NTE proteins. The present invention further provides assays for the detection of NTE polymorphisms and mutations associated with disease states, as well as methods of screening for therapeutic agents, ligands, and modulators of NTE proteins.

In certain embodiments, the present invention provides a method for diagnosing a motor neuron disorder, comprising detecting the presence of a polymorphism associated with NTE gene in a sample. In preferred embodiments, the motor neuron disorder is selected from the group consisting of amyotrophic lateral sclerosis, autosomal recessive spastic paraplegia, hereditary spastic paraplegia, primary lateral sclerosis, progressive pseudobulbar palsy, progressive muscular atrophy, progressive bulbar palsy, and postpolio syndrome.

In preferred embodiments, the polymorphism is in the coding region of the NTE gene. In some preferred embodiments, the detecting comprises detecting the polymorphism in a nucleic acid from the sample. In some preferred embodiments, the sample is DNA. In other preferred embodiments, the sample is RNA. In preferred embodiments, the detecting comprises detecting a polymorphic protein. In other preferred embodiments, the detecting a polymorphic protein occurs with an antibody. In further preferred embodiments, the polymorphic protein comprises an amino acid change M to V at position 1012.

In certain embodiments, the present invention provides a method for identifying an individual at risk for toxicity resulting from organophosphate exposure, comprising detecting the presence of a polymorphism associated with NTE gene in a sample. In preferred embodiments, the organophosphate is selected from the group consisting of disulfoton, phorate, dimethoate, ciodrin, dichlorvos, dioxathion, ruelene, carbophenothion, supona, hexaethyl tetraphosphate, tetraethyl pyrophosphate, octamethyl pyrophosphoramide, ethyl p-nitrophenyl thionobenzenephosphonate, parathion, malathion, ronnel, coumaphos, diazinon, trichlorfon, paraoxon, potasan, dimefox, mipafox, schradan, sevin, chlorpyrifos, dimeton, sarin, soman, tabun, cyclohexyl methylphosphonofluoridate, and O-ethyl S-diisopropylaminomethyl methylphosphonothiolate. In preferred embodiments, the polymorphism is in the coding region of the NTE gene. In other preferred embodiments, the detecting comprises detecting the polymorphism in a nucleic acid from the sample. In some preferred embodiments, the sample is DNA. In other preferred embodiments, the sample is RNA. In preferred embodiments, the detecting comprises detecting a polymorphic protein. In other preferred embodiments, the detecting a polymorphic protein occurs with an antibody. In further preferred embodiments, the polymorphic protein comprises an amino acid change M to V at position 1012.

In certain embodiments, the present invention provides a composition comprising an isolated and purified nucleic acid sequence encoding a protein selected from the group consisting of SEQ ID NOs: 5 and 6. In preferred embodiments, the sequence is operably linked to a heterologous promoter. In other preferred embodiments, the sequence is contained within a vector. In some embodiments, the vector is within a host cell.

In preferred embodiments, the nucleic acid is selected from the group consisting of SEQ ID NO: 1 and variants thereof that are at least 80% (e.g., 90%, 95%, 99%, . . . ) identical to a sequence selected from the group consisting of SEQ ID NO: 2, SEQ ID NO: 3 and SEQ ID NO: 4. In preferred embodiments, the nucleic acid sequence is selected from the group consisting of SEQ ID NOs: 1, 2, 3 and 4. In some embodiments, the variant has one or more (e.g., 2, 3, 4, . . . ) mismatches as compared to SEQ ID NOs: 1, 2, 3, and 4.

In certain embodiments, the present invention provides a composition comprising a polypeptide having an amino acid sequence selected from the group consisting of SEQ ID NOs: 5 and 6 and variants thereof that are at least 80% identical to SEQ ID NOs: 5 and 6, 90% identical to SEQ ID NOs: 5 and 6, 95% identical to SEQ ID NOs: 5 and 6, and/or 99% identical to SEQ ID NOs: 5 and 6.

In certain embodiments, the present invention provides a method of reducing NTE activity comprising providing i) a target cell expressing NTE protein; and ii) an agent that inhibits NTE expression or activity; b) contacting the target cell with the composition thereby reducing NTE expression or activity. In preferred embodiments, the agent comprises a composition comprising a small interfering RNA duplex (siRNA), or a vector encoding the siRNA, that targets the NTE mRNA. In preferred embodiments, the target cell is a neurological cell. In other preferred embodiments, the contacting is conducted in vitro. In yet other preferred embodiments, the contacting is conducted under conditions such the vector expresses the siRNA in the target cell. In preferred embodiments, the composition further comprises a nucleic acid transfecting agent. In some embodiments, the agent is an antibody (e.g., specific for wild-type or mutant NTE). The method may be used for research, drug screening, diagnostic, and therapeutic applications.

In certain embodiments, the present invention provides a method for producing variants of NTE comprising a) providing a nucleic acid sequence selected from the group consisting of SEQ ID NOs: 1, 2, 3 and 4; b) mutagenizing the nucleic acid sequence; and c) screening the variant for NTE activity.

In certain embodiments, the present invention provides a method for screening compounds for the ability to alter NTE activity, comprising a) providing i) a polypeptide sequence comprising at least a portion of NTE; ii) one or more test compounds; b) combining in any order, the polypeptide sequence comprising at least a portion of NTE, and the one or more test compounds under conditions such that the polypeptide sequence, and the test compound interact; and c) measuring NTE activity.

In certain embodiments, the present invention provides a method for identifying pharmaceutical agents useful for treating hereditary spastic paraplegias, comprising a) providing i. target cells, wherein the target cells comprise NTE polypeptide; ii. a candidate pharmaceutical agent; and b) exposing the target cells to the candidate pharmaceutical agents; c) measuring the activity of the NTE polypeptide of the target cells; and d) selecting candidate pharmaceutical agents that inhibit the activity of the NTE polypeptide.

In certain embodiments, the present invention provides a method for producing NTE-positive neurons, comprising the steps of: a) providing a human embryonic stem cell line; and b) contacting the embryonic stem cell line with a solution comprising at least one soluble molecule expressed by fetal striatal cells, under conditions suitable for producing NTE-positive neurons. In preferred embodiments, the fetal striatal cells are astrocytes. In some preferred embodiments, the fetal striatal cells are cocultured with the human embryonic stem cell line. In preferred embodiments, the at least one soluble molecule comprises glial-derived neurotrophic factor.

In certain embodiments, the present invention provides methods of alleviating motor neuron disorder related symptoms in a patient with a motor neuron disorder comprising: a) providing a cell culture produced by a method comprising contacting a human embryonic stem cell line with at least one soluble molecule expressed by fetal striatal cells, under conditions suitable for producing NTE-positive neurons; and b) administering the cultured cells comprising NTE-positive neurons to the brain of a patient with a motor neuron disorder, under conditions suitable for alleviating motor neuron disorder symptoms. In preferred embodiments, the at least one soluble molecule comprises glial-derived neurotrophic factor.

DESCRIPTION OF THE FIGURES

FIG. 1A and B shows the nucleic acid sequence of NTE (SEQ ID NO: 1).

FIG. 2A and B shows a variant nucleic acid sequence of NTE (SEQ ID NO: 2).

FIG. 3A and B shows a variant nucleic acid sequence of NTE (SEQ ID NO: 3).

FIG. 4A and B shows a variant nucleic acid sequence of NTE (SEQ ID NO: 4)

FIG. 5 shows the amino acid sequence of NTE (SEQ ID NO: 5).

FIG. 6 shows a variant amino acid sequence of NTE (SEQ ID NO: 6).

Definitions

To facilitate understanding of the invention, a number of terms are defined below.

As used herein, the term "NTE" when used in reference to a protein or nucleic acid refers to a NTE protein or nucleic acid encoding a NTE protein of the present invention. The term NTE encompasses both proteins that are identical to wild-type NTEs and those that are derived from wild type NTE (e.g., variants of NTE polypeptides of the present invention) or chimeric genes constructed with portions of NTE coding regions). In some embodiments, the "NTE" is a wild type NTE nucleic acid (SEQ ID NO: 1) or amino acid (SEQ ID NO: 5) sequence. In other embodiments, the "NTE" is a variant or mutant nucleic acid (SEQ ID NO: 2, 3, 4) or amino acid (SEQ ID NO: 6).

As used herein, the terms "subject" and "patient" refer to any animal, such as a mammal like a dog, cat, bird, livestock, and preferably a human. Specific examples of "subjects" and "patients" include, but are not limited to, individuals with a motor neuron disorder, and individuals with motor neuron disorder-related characteristics or symptoms.

As used herein, the term "motor neuron disorder" refers to disorders of the motor nerves of the brain and/or spinal chord, including, but not limited to progressive deterioration of the motor nerves in the spinal chord and/or brain. Examples of motor neuron disorders include, but are not limited to, amyotrophic lateral sclerosis, hereditary spastic paraplegia (HSP), primary lateral sclerosis, progressive pseudobulbar palsy, progressive muscular atrophy, progressive bulbar palsy, and postpolio syndrome.

As used herein, the phrase "symptoms of motor neuron disorder" and "characteristics of motor neuron disorder" include, but are not limited to, lower extremity weakness, bladder disturbance, impaired position sense in the legs, and neurologic deficits.

As used herein, the term "organophosphate" refers to compounds capable of irreversibly binding with cholinesterase. Examples of organophosphates include, but are not limited to, disulfoton, phorate, dimethoate, ciodrin, dichlorvos, dioxathion, ruelene, carbophenothion, supona, hexaethyl tetraphosphate, tetraethyl pyrophosphate, octamethyl pyrophosphoramide, ethyl p-nitrophenyl thionobenzenephosphonate, parathion, malathion, ronnel, coumaphos, diazinon, trichlorfon, paraoxon, potasan, dimefox, mipafox, schradan, sevin, chlorpyrifos, dimeton, and chemical warfare agents (e.g., sarin, soman, tabun, cyclohexyl methylphosphonofluoridate, O-ethyl S-diisopropylaminomethyl methylphosphonothiolate).

As used herein, the term "chemical warfare" refers to the use of agents capable of injuring or killing or incapacitating a subject. Examples of chemical warfare include, but are not limited to, agents capable of irreversibly binding with cholinesterase.

As used herein, the terms "organophosphate toxicity" or "chemical warfare symptoms" or related terms, refer to compounds capable of irreversibly binding to cholinesterase, resulting in the phosphorylation and deactivation of acetylcholinesterase. The subsequent accumulation of acetylcholine at the neural synapse causes an initial overstimulation, followed by eventual exhaustion and disruption of postsynaptic neural transmission in the central nervous system (CNS) and peripheral nervous systems (PNS).

As used herein, the terms "organophosphate toxicity symptoms" or "organophosphate symptoms" or "germ warfare symptoms" or "organophosphate toxicity clinical symptoms" or related terms, include, but are not limited to, excess salivation, lacrimation, abdominal pain, vomiting, intestinal hypermotility, diarrhea, bronchoconstriction, an increase in bronchial secretions, involuntary irregular, violent muscle contractions and weakness of voluntary muscles, respiratory failure, weight loss, muscular weakness, pulmonary edema, asphyxia, gastroenteritis, seizure, and kidney and liver degeneration.

The phrase "under conditions such that the symptoms are reduced" refers to any degree of qualitative or quantitative reduction in detectable symptoms of motor neuron disorders, including but not limited to, a detectable impact on the rate of recovery from disease, or the reduction of at least one symptom of a motor neuron disorder.

As used herein, the term "instructions for using said kit for said detecting the presence or absence of a variant NTE nucleic acid or polypeptide in said biological sample" includes instructions for using the reagents contained in the kit for the detection of variant and wild type NTE nucleic acids or polypeptides. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., NTE). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "NTE gene" or "NTE genes" refers to the full-length NTE nucleotide sequence (e.g., contained in SEQ ID NOs: 1, 2, 3, 4). However, it is also intended that the term encompass fragments of the NTE sequences, mutants of the NTE sequences, as well as other domains within the full-length NTE nucleotide sequences. Furthermore, the terms "NTE nucleotide sequence" or "NTE polynucleotide sequence" encompasses DNA sequences, cDNA sequences, RNA (e.g., mRNA) sequences, and associated regulatory sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Complementarity can include the formation of base pairs between any type of nucleotides, including non-natural bases, modified bases, synthetic bases and the like.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G: C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The present invention is not limited to the hybridization of probes of about 500 nucleotides in length. The present invention contemplates the use of probes between approximately 10 nucleotides up to several thousand (e.g., at least 5000) nucleotides in length. One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (U.S.A.) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., NTE).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., a NTE gene of the present invention).

As used herein, the term "detection assay" refers to an assay for detecting the presence or absence of variant nucleic acid sequences (e.g., polymorphisms or mutations) in a given allele of a particular gene (e.g., a NTE gene). Examples of suitable detection assays include, but are not limited to, those described below in Section III B.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding NTE includes, by way of example, such nucleic acid in cells ordinarily expressing NTE where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, NTE antibodies are purified by removal of contaminating non-immunoglobulin proteins; they are also purified by the removal of immunoglobulin that does not bind a NTE polypeptide. The removal of non-immunoglobulin proteins and/or the removal of immunoglobulins that do not bind a NTE polypeptide results in an increase in the percent of NTE-reactive immunoglobulins in the sample. In another example, recombinant NTE polypeptides are expressed in bacterial host cells and the polypeptides are purified by the removal of host cell proteins; the percent of recombinant NTE polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein, is used to indicate a protein that does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 [1989]).

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding NTEs (e.g., SEQ ID NOs: 1, 2, 3, 4) or fragments thereof may be employed as hybridization probes. In this case, the NTE encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

DETAILED DESCRIPTION OF THE INVENTION

Neuropathy Target Esterase (NTE) is involved in neuronal development and is the target for neurodegeneration induced by selected organophosphorus pesticides and chemical warfare agents. NTE is an integral membrane protein present in all neurons and in some non-neural-cell types of vertebrates. NTE is involved in a cell-signaling pathway controlling interactions between neurons and accessory glial cells in the developing nervous system. NTE has serine esterase activity and efficiently catalyses the hydrolysis of phenyl valerate (PV) in vitro. By sequence analysis NTE is related neither to the major serince esterase family, which included acetylcholinesterase, nor to any other known serine hydrolases. NTE comprises at least two functional domains: an N-terminal putative regulatory domain and a C-terminal effector domain which contains the esterase activity and is, in part, conserved in proteins found in bacteria, yeast, nematodes and insects. NTE's effector domain contains three predicted transmembrane segments, and the active-site serine residue lies at the center of one of these segments. The isolated recombinant domain shows PV hydrolase activity only when incorporated into phospholipid liposomes.

Mice generated with disruption in Nte (e.g., Nte−/−) mice died after embryonic day 8, and heterozygous Nte+/− mice had lower activity of Nte in the brain and higher mortality when exposed to an Nte-inhibiting compound (EOPF) than did wildtype mice, while Nte+/− and wildtype mice treated with 1 mg per kg of body weight of EOPF had elevated motor activity, indicating that even minor reduction of Nte activity leads to neurological disease (see, e.g., Winrow, C. J., et al., (2003) Nature Genetics 33: 477-486; herein incorporated by reference in its entirety). Additionally, studies indicate that genetic or chemical reduction of Nte activity results in a motor neuron disorder phenotype (see, e.g., Bargal, R., et al., (2000) Nature Genetics 26: 120-123; Lush, M. J., et al., (1998) Biochem. J. 332: 1-4; Moser, M., et al., (2004) Molec. Cell. Biol. 24: 1667-1679; O'Callaghan, J. P. (2003) Nature Genetics 33: 437-438; each herein incorporated by reference in their entirities).

The present invention relates to the NTE proteins and nucleic acids encoding the NTE proteins. The present invention further provides assays for the detection of therapeutic agents, and for the detection of NTE polymorphisms and mutations associated with disease states. Exemplary embodiments of the present invention are described in more detail in the following sections: I. NTE Polynucleotides; II. NTE Polypeptides; III. Detection of NTE Alleles; IV. Generation of NTE Antibodies; V. Gene Therapy Using NTE; VI. Transgenic Animals Expressing Exogenous NTE Genes and Homologs, Mutants, and Variants Thereof; VII. Drug Screening Using NTE; VIII. Pharmaceutical Compositions Containing NTE Nucleic Acid, Peptides, and Analogs; IX. Mutations Within the NTE Gene Result in Motor Neuron Disorders; and X. Mutations Within NTE Gene Result in Susceptibility to Organophosphate Toxicity.

I. NTE Polynucleotides

As described above, the present invention provides novel NTE family genes. Accordingly, the present invention provides nucleic acids encoding NTE genes, homologs, variants (e.g., polymorphisms and mutants), including but not limited to, those described in SEQ ID NOs: 1-4. Table 1 describes exemplary NTE genes of the present invention. In some embodiments, the present invention provides polynucleotide sequences that are capable of hybridizing to SEQ ID NOs: 1-4 under conditions of low to high stringency as long as the polynucleotide sequence capable of hybridizing encodes a protein that retains a biological activity of the naturally occurring NTEs. In some embodiments, the protein that retains a biological activity of naturally occurring NTE is 70% homologous to wild-type NTE, preferably 80% homologous to wild-type NTE, more preferably 90% homologous to wild-type NTE, and most preferably 95% homologous to wild-type NTE. In preferred embodiments, hybridization conditions are based on the melting temperature ($T_m$) of the nucleic acid binding complex and confer a defined "stringency" as explained above (See e.g., Wahl, et al., Meth. Enzymol., 152:399-407 [1987], incorporated herein by reference).

In other embodiments of the present invention, additional alleles of NTE genes are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Examples of the alleles of the present invention include that encoded by SEQ ID NO: 1 (wild type) and disease alleles thereof (e.g., SEQ ID NOs: 2-4). Additional examples include truncation mutations (e.g., such that the encoded mRNA does not produce a complete protein).

In still other embodiments of the present invention, the nucleotide sequences of the present invention may be engineered in order to alter an NTE coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of NTE may be extended utilizing the nucleotide sequence in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318-22 [1993]). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 [1991]). The PROMOTER-FINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed NTE sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., NTE function) for such purposes as altering the biological activity (e.g., altered NTE function). Such modified peptides are considered functional equivalents of peptides having an activity of a NTE peptide as defined herein. A modified peptide can be produced in which the nucleotide sequence encoding the polypeptide has been altered, such as by substitution, deletion, or addition. In particularly preferred embodiments, these modifications do not significantly reduce the biological activity of the modified NTE genes. In other words, construct "X" can be evaluated in order to determine whether it is a member of the genus of modified or variant NTE's of the present invention as defined functionally, rather than structurally. In preferred embodiments, the activity of variant NTE polypeptides is evaluated by methods described herein (e.g., the generation of transgenic animals or the use of signaling assays).

Moreover, as described above, variant forms of NTE genes are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of NTE disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a NTE coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

TABLE 1

| | NTE Genes | |
|---|---|---|
| NTE Gene | SEQ ID NO (Nucleic acid) | SEQ ID NO (Polypeptide) |
| NTE | 1 | 5 |
| NTE*3034 | 2 | 6 |
| NTE*2944-2947 | 3 | x |
| NTE*2953 | 4 | x |

II. NTE Polypeptides

In other embodiments, the present invention provides NTE polynucleotide sequences that encode NTE polypeptide sequences (e.g., the polypeptides of SEQ ID NOs: 5 and 6). Other embodiments of the present invention provide fragments, fusion proteins or functional equivalents of these NTE proteins. In some embodiments, the present invention provides mutants of NTE polypeptides. In still other embodiments of the present invention, nucleic acid sequences corresponding to NTE variants, homologs, and mutants may be used to generate recombinant DNA molecules that direct the expression of the NTE variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NOs: 1-4 that encode substantially the same or a functionally equivalent amino acid sequence, may be used to clone and express NTE. In general, such polynucleotide sequences hybridize to SEQ ID NOs: 1-4 under conditions of high to medium stringency as described above. As will be understood by those of skill in the art, it may be advantageous to produce NTE-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of NTE expression or to produce recombinant RNA transcripts having desirable properties, such as a longer half-life, than transcripts produced from naturally occurring sequence.

1. Vectors for Production of NTE

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 1-4). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NOs: 1-4) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of genes in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of NTE Polypeptides

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli*, *Salmonella typhimurium*, *Bacillus subtilis*, and various species within the genera *Pseudomonas*, *Streptomyces*, and *Staphylococcus*, as well as *Saccharomycees cerivisiae*, *Schizosaccharomycees pombe*, *Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of NTE Polypeptides

The present invention also provides methods for recovering and purifying NTE polypeptides from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having a coding sequence of a NTE gene (e.g., SEQ ID NOs: 1-4) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of NTE Polypeptide

In addition, the present invention provides fragments of NTE polypeptides (i.e., truncation mutants). In some embodiments of the present invention, when expression of a portion of the NTE protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751 [1987]) and *Salmonella typhimurium* and its in vitro activity has been demonstrated on recombinant proteins (Miller et al., Proc. Natl. Acad. Sci. USA 84:2718 [1990]). Therefore, removal of an N-terminal methionine, if desired, can be achieved either in vivo by expressing such recombinant polypeptides in a host which produces MAP (e.g., *E. coli* or CM89 or *S. cerivisiae*), or in vitro by use of purified MAP.

5. Fusion Proteins Containing NTE

The present invention also provides fusion proteins incorporating all or part of the NTE polypeptides of the present invention. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a NTE protein. In some embodiments of the present invention, the VP6 capsid protein of rotavirus is used as an immunologic carrier protein for portions of a NTE polypeptide, either in the monomeric form or in the form of a viral particle. In other embodiments of the present invention, the nucleic acid sequences corresponding to the portion of a NTE polypeptide against which antibodies are to be raised can be incorporated into a fusion gene construct which includes coding sequences for a late vaccinia virus structural protein to produce a set of recombinant viruses expressing fusion proteins comprising a portion of NTE as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of a NTE polypeptide and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of NTE is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the NTE proteins can also be expressed and presented by bacterial cells.

In addition to utilizing fusion proteins to enhance immunogenicity, it is widely appreciated that fusion proteins can also facilitate the expression of proteins, such as a NTE protein of the present invention. Accordingly, in some embodiments of the present invention, NTE polypeptides can be generated as glutathione-S-transferase (i.e., GST fusion proteins). It is contemplated that such GST fusion proteins will enable easy purification of NTE polypeptides, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of a NTE polypeptide, can allow purification of the expressed NTE fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of NTE

Still other embodiments of the present invention provide mutant or variant forms of NTE polypeptides (i.e., muteins). It is possible to modify the structure of a peptide having an activity of a NTE polypeptide of the present invention for such purposes as enhancing therapeutic or prophylactic efficacy, disabling the protein, or stability (e.g., ex vivo shelf life, and/or resistance to proteolytic degradation in vivo). Such modified peptides are considered functional equivalents of peptides having an activity of the subject NTE proteins as defined herein. A modified peptide can be produced in which the amino acid sequence has been altered, such as by amino acid substitution, deletion, or addition.

Moreover, as described above, variant forms (e.g., mutants or polymorphic sequences) of the subject NTE proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present NTE proteins, as well as truncation mutants, and is especially useful for identifying potential variant sequences (i.e., mutants or polymorphic sequences) that are involved in neurological disorders (e.g., motor neuron disorders) or resistance to neurological disorders. The purpose of screening such combinatorial libraries is to generate, for example, novel NTE variants that can act as either agonists or antagonists, or alternatively, possess novel activities all together.

Therefore, in some embodiments of the present invention, NTE variants are engineered by the present method to provide altered (e.g., increased or decreased) biological activity. In other embodiments of the present invention, combinatorially-derived variants are generated which have a selective potency relative to a naturally occurring NTE.

Such proteins, when expressed from recombinant DNA constructs, can be used in gene therapy protocols.

Still other embodiments of the present invention provide NTE variants that have intracellular half-lives dramatically different than the corresponding wild-type protein. For example, the altered protein can be rendered either more stable or less stable to proteolytic degradation or other cellular process that result in destruction of, or otherwise inactivate NTE polypeptides. Such variants, and the genes which encode them, can be utilized to alter the location of NTE expression by modulating the half-life of the protein. For instance, a short half-life can give rise to more transient NTE biological effects and, when part of an inducible expression system, can allow tighter control of NTE levels within the cell. As above, such proteins, and particularly their recombinant nucleic acid constructs, can be used in gene therapy protocols.

In still other embodiments of the present invention, NTE variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of NTE homologs, variants or other related proteins are aligned, preferably to promote the highest homology possible. Such a population of variants can include, for example, NTE homologs from one or more species, or NTE variants from the same species but which differ due to mutation or polymorphisms. Amino acids that appear at each position of the aligned sequences are selected to create a degenerate set of combinatorial sequences.

In a preferred embodiment of the present invention, the combinatorial NTE library is produced by way of a degenerate library of genes encoding a library of polypeptides which each include at least a portion of potential NTE protein sequences. For example, a mixture of synthetic oligonucleotides can be enzymatically ligated into gene sequences such that the degenerate set of potential NTE sequences are expressible as individual polypeptides, or alternatively, as a set of larger fusion proteins (e.g., for phage display) containing the set of NTE sequences therein.

There are many ways by which the library of potential NTE homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential NTE sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; each of which is herein incorporated by reference; as well as U.S. Pat. Nos. 5,223,409, 5,198,346, and 5,096,815; each of which is incorporated herein by reference).

It is contemplated that the NTE nucleic acids of the present invention (e.g., SEQ ID NOs: 1-4, and fragments and variants thereof) can be utilized as starting nucleic acids for directed evolution. These techniques can be utilized to develop NTE variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1: 17-24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for NTE activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for NTE activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of NTE homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of NTE Polypeptides

In an alternate embodiment of the invention, the coding sequence of NTE is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 [1981]). In other embodiments of the present invention, the protein itself is produced using chemical methods to synthesize either an entire NTE amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example, using ABI 431 A Peptide Synthesizer (Perkin Elmer) in accordance with the instructions provided by the manufacturer. Additionally, the amino acid sequence of a NTE polypeptide, or any part thereof, may be altered during direct synthesis and/or combined using chemical methods with other sequences to produce a variant polypeptide.

III. Detection of NTE Alleles

In some embodiments, the present invention provides methods of detecting the presence of wild type or variant (e.g., mutant or polymorphic) NTE nucleic acids or polypeptides. The detection of mutant NTE polypeptides finds use in the diagnosis of disease (e.g., motor neuron disorder).

A. Detection of Variant NTE Alleles

In some embodiments, the present invention provides alleles of NTE that increase a patient's susceptibility to neurological disorders (e.g., hereditary spastic paraplegias). Any mutation that results in an altered phenotype (e.g., progressive spastic weakness in the legs; wasting of intrinsic muscles of the distal upper and lower extremity muscles; peripheral motor axonopathy; spinal chord atrophy) is within the scope of the present invention.

Accordingly, the present invention provides methods for determining whether a patient has an increased susceptibility to neurological disorders (e.g., HSP) by determining, directly or indirectly, whether the individual has a variant NTE allele. In other embodiments, the present invention provides methods for providing a prognosis of increased risk for motor neuron disorder to an individual based on the presence or absence of one or more variant alleles of NTE.

A number of methods are available for analysis of variant (e.g., mutant or polymorphic) nucleic acid or polypeptide sequences. Assays for detection variants (e.g., polymorphisms or mutations) via nucleic acid analysis fall into several categories including, but not limited to, direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following exemplary assays are useful in the present invention: directs sequencing assays, PCR assays, mutational analysis by dHPLC (e.g., available from Transgenomic, Omaha, Nebr. or Varian, Palo Alto, Calif.), fragment length polymorphism assays (e.g., RFLP or CFLP (See e.g. U.S. Pat. Nos. 5,843,654; 5,843,669; 5,719,208; and 5,888,780; each of which is herein incorporated by reference)), hybridization assays (e.g., direct detection of hybridization, detection of hybridization using DNA chip assays (See e.g., U.S. Pat. Nos. 6,045,996; 5,925,525; 5,858,659; 6,017,696; 6,068,818; 6,051,380; 6,001,311; 5,985,551; 5,474,796; PCT Publications WO 99/67641 and WO 00/39587, each of which is herein incorporated by reference), enzymatic detection of hybridization (See e.g., U.S. Pat. Nos. 5,846,717, 6,090,543; 6,001,567; 5,985,557; 5,994,069; 5,962,233; 5,538,848; 5,952,174 and 5,919,626, each of which is herein incorporated by reference)), polymorphisms detected directly or indirectly (e.g., detecting sequences (other polymorphisms) that are in linkage disequilibrium with the polymorphism to be indentified; for example, other sequences in the NTE locus may be used; this method is described in U.S. Pat. No.: 5,612,179 (herein incorporated by reference)) and mass spectrometry assays.

In addition, assays for the detection of variant NTE proteins find use in the present invention (e.g., cell free translation methods, See e.g., U.S. Pat. No. 6,303,337, herein incorporated by reference) and antibody binding assays. The generation of antibodies that specifically recognize mutant versus wild type proteins are discussed below.

B. Kits for Analyzing Risk of Neurological Disorders

The present invention also provides kits for determining whether an individual contains a wild-type or variant (e.g., mutant or polymorphic) allele or polypeptide of NTE. In some embodiments, the kits are useful determining whether the subject is at risk of developing a neurological disorder (e.g., HSP). The diagnostic kits are produced in a variety of ways. In some embodiments, the kits contain at least one reagent for specifically detecting a mutant NTE allele or protein. In preferred embodiments, the reagent is a nucleic acid that hybridizes to nucleic acids containing the mutation and that does not bind to nucleic acids that do not contain the mutation. In other embodiments, the reagents are primers for amplifying the region of DNA containing the mutation. In still other embodiments, the reagents are antibodies that preferentially bind either the wild-type or mutant NTE proteins.

In some embodiments, the kit contains instructions for determining whether the subject is at risk for a neurological disorder (e.g, NTE related disease). In preferred embodiments, the instructions specify that risk for developing a motor neuron disorder is determined by detecting the presence or absence of a mutant NTE allele in the subject, wherein subjects having an mutant allele are at greater risk for developing a spastic paraplegia disease.

The presence or absence of a disease-associated mutation in a NTE gene can be used to make therapeutic or other medical decisions. For example, couples with a family history of NTE related diseases may choose to conceive a child via in vitro fertilization and pre-implantation genetic screening. In this case, fertilized embryos are screened for mutant (e.g., disease associated) alleles of a NTE gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a NTE allele known to be associated with a motor neuron disorder allows for early intervention (e.g., genetic or pharmaceutical therapies).

In some embodiments, the kits include ancillary reagents such as buffering agents, nucleic acid stabilizing reagents, protein stabilizing reagents, and signal producing systems (e.g., florescence generating systems as Fret systems). The test kit may be packaged in any suitable manner, typically with the elements in a single container or various containers as necessary along with a sheet of instructions for carrying out the test. In some embodiments, the kits also preferably include a positive control sample.

C. Bioinformatics

In some embodiments, the present invention provides methods of determining an individual's risk of developing a neurological disorder (e.g., HSP) based on the presence of one or more variant alleles of a NTE gene. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting an NTE related motor neuron disorder associated with a given polymorphism, as well as the sequences). In some embodiments, one of the computers stores application programs (e.g., for analyzing the results of detection assays). Results are then delivered to the user (e.g., via one of the computers or via the internet).

For example, in some embodiments, a computer-based analysis program is used to translate the raw data generated by the detection assay (e.g., the presence, absence, or amount of a given NTE allele or polypeptide) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant NTE genes or polypeptides), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing an NTE related motor neuron disorder) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the association of a given NTE allele with motor neuron disorders.

IV. Generation of NTE Antibodies

The present invention provides isolated antibodies or antibody fragments (e.g., FAB fragments). Antibodies can be generated to allow for the detection of a NTE proteins (e.g., wild type or mutant) of the present invention. The antibodies may be prepared using various immunogens. In one embodiment, the immunogen is a human NTE peptide to generate antibodies that recognize human NTE. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against a NTE polypeptide. For the production of antibody, various host animals can be immunized by injection with the peptide corresponding to the NTE epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward NTE, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, NY). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in *Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing NTE specific single chain antibodies. An additional embodiment of the invention utilizes the techniques described for the construction of Fab expression libraries (Huse et al., Science 246:1275-1281 [1989]) to allow rapid and easy identification of monoclonal Fab fragments with the desired specificity for a NTE polypeptide.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., N.Y.; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immudiffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.) The foregoing antibodies can be used in methods known in the art relating to the localization and structure of NTE (e.g., for Western blotting), measuring levels thereof in appropriate biological samples, etc. The antibodies can be used to detect a NTE in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of a human NTE using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of NTE detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of NTE or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of NTE. Such antibodies can also be used diagnostically to measure abnormal expression of NTE, or the aberrant formation of protein complexes, which may be indicative of a disease state.

V. Gene Therapy Using NTE

The present invention also provides methods and compositions suitable for gene therapy to alter NTE expression, production, or function. As described above, the present invention provides human NTE genes and provides methods of obtaining NTE genes from other species. Thus, the methods described below are generally applicable across many species. In some embodiments, it is contemplated that the gene therapy is performed by providing a subject with a wild-type allele of a NTE gene (i.e., an allele that does not contain a NTE disease allele (e.g., free of disease causing polymorphisms or mutations)). Subjects in need of such therapy are identified by the methods described above. In some embodiments, transient or stable therapeutic nucleic acids are used (e.g., antisense oligonucleotides, siRNAs) to reduce or prevent expression of mutant proteins.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No., 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus") MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

VI. Transgenic Animals Expressing Exogenous NTE Genes and Homologs, Mutants, and Variants Thereof The present invention contemplates the generation of transgenic animals comprising an exogenous NTE gene or homologs, mutants, or variants thereof. In preferred embodiments, the transgenic animal displays an altered phenotype as compared to wild-type animals. In some embodiments, the altered phenotype is the overexpression of mRNA for a NTE gene as compared to wild-type levels of NTE expression. In other embodiments, the altered phenotype is the decreased expression of mRNA for an endogenous NTE gene as compared to wild-type levels of endogenous NTE expression. In some preferred embodiments, the transgenic animals comprise mutant alleles of NTE. Methods for analyzing the presence or absence of such phenotypes include Northern blotting, mRNA protection assays, and RT-PCR. In other embodiments, the transgenic mice have a knock out mutation of a NTE gene. In preferred embodiments, the transgenic animals display an altered susceptibility to neurological disorders (e.g., HSP).

Such animals find use in research applications (e.g., identifying signaling pathways that a NTE protein is involved in), as well as drug screening applications (e.g., to screen for drugs that prevent or treat motor neuron disorders). For example, in some embodiments, test compounds (e.g., a drug that is suspected of being useful to treat a neurological disorder) are administered to the transgenic animals and control animals with a wild type NTE allele and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which a particular domain of a NTE is deleted). Methods for homologous recombination are described in U.S. Pat. No. 5,614,396, incorporated herein by reference.

VII. Drug Screening Using NTE

In some embodiments, the isolated nucleic acid and polypeptides of NTE genes of the present invention (e.g., SEQ ID NOS: 1-4) and related proteins and nucleic acids are used in drug screening applications for compounds that alter (e.g., enhance or inhibit) NTE activity and signaling. The present invention further provides methods of identifying ligands and signaling pathways of the NTE proteins of the present invention.

The present invention is not limited to a particular mechanism. Indeed, an understanding of the mechanism is not necessary to practice the present invention. Nonetheless, based upon a hydrophobicity analysis of NTE family proteins (see Chai et al, Am J Hum Genet (2003 in press)), it is contemplated that NTE family proteins function as receptors or transporters.

In some embodiments, the present invention provides methods of screening compounds for the ability to alter NTE activity mediated by natural ligands (e.g., identified using the methods described above). Such compounds find use in the treatment of disease mediated by NTE family members (e.g., motor neuron disorders).

In some embodiments, the present invention provides methods of screening compounds for an ability to interact with mutant NTE nucleic acid (e.g., SEQ ID NOs: 2-4) and/or mutant NTE polypeptides (e.g., SEQ ID NO: 6), while simultaneously not interacting with wild type NTE nucleic acid (e.g., SEQ ID NO: 1) and/or wild type NTE polypeptides (e.g., SEQ ID NO: 5). Such compounds find use in the treatment of neurological disorders facilitated by the presence of mutant forms of NTE nucleic acids and/or proteins.

In one screening method, the two-hybrid system is used to screen for compounds (e.g., proteins) capable of altering NTE function(s) (e.g., interaction with a binding partner) in vitro or in vivo. In one embodiment, a GAL4 binding site, linked to a reporter gene such as lacZ, is contacted in the presence and absence of a candidate compound with a GAL4 binding domain linked to a NTE fragment and a GAL4 transactivation domain II linked to a binding partner fragment. Expression of the reporter gene is monitored and a decrease in the expression is an indication that the candidate compound inhibits the interaction of a NTE with the binding partner. Alternately, the effect of candidate compounds on the interaction of a NTE with other proteins (e.g., proteins known to interact directly or indirectly with the binding partner) can be tested in a similar manner In some embodiments, the present invention provides methods of identifying NTE binding partners or ligands that utilize immunoprecipitation. In some embodiments, antibodies to NTE proteins are utilized to immunoprecipitated NTEs and any bound proteins. In other embodiments, NTE fusion proteins are generated with tags and antibodies to the tags are utilized for immunoprecipitation. Potential binding partners that immunoprecipitate with NTEs can be identified using any suitable method.

In another screening method, candidate compounds are evaluated for their ability to alter NTE activity by contacting NTE, binding partners, binding partner-associated proteins, or fragments thereof, with the candidate compound and determining binding of the candidate compound to the peptide. The protein or protein fragments is/are immobilized using methods known in the art such as binding a GST-NTE fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al, Gene 67:31 [1988]). The fusion construct is then transformed into a suitable expression system (e.g., *E. coli* XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate NTE physiological effects (e.g., NTE related disorders).

In another screening method, one of the components of the NTE/binding partner signaling system is immobilized. Polypeptides can be immobilized using methods known in the art, such as adsorption onto a plastic microtiter plate or specific binding of a GST-fusion protein to a polymeric bead containing glutathione. For example, in some embodiments, GST-NTE is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of NTE with the other peptide. A variation of this method allows for the screening of compounds that are capable of disrupting a previously-formed protein/protein complex. For example, in some embodiments a complex comprising a NTE or a NTE fragment bound to another peptide is immobilized as described above and contacted with a candidate compound. The dissolution of the complex by the candidate compound correlates with the ability of the compound to disrupt or inhibit the interaction between NTE and the other peptide.

Another technique for drug screening provides high throughput screening for compounds having suitable binding affinity to NTE peptides and is described in detail in WO 84/03564, incorporated herein by reference. Briefly, large numbers of different small peptide test compounds are synthesized on a solid substrate, such as plastic pins or some other surface. The peptide test compounds are then reacted with NTE peptides and washed. Bound NTE peptides are then detected by methods well known in the art.

Another technique uses NTE antibodies, generated as discussed above. Such antibodies are capable of specifically binding to NTE peptides and compete with a test compound for binding to NTE. In this manner, the antibodies can be used to detect the presence of any peptide that shares one or more antigenic determinants of a NTE peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with NTE genes and variants thereof for screening compounds for activity, and in particular for high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding NTE or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by NTE in operable association with a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

Specifically, the present invention provides screening methods for identifying modulators, i.e., candidate or test compounds or agents (e.g., proteins, peptides, peptidomimetics, peptoids, small molecules or other drugs) which bind to a NTE of the present invention, have an inhibitory (or stimulatory) effect on, for example, NTE expression or NTE activity, or have a stimulatory or inhibitory effect on, for example, the expression or activity of a NTE substrate. Compounds thus identified can be used to modulate the activity of target gene products (e.g., NTE genes) either directly or indirectly in a therapeutic protocol, to elaborate the biological function of the target gene product, or to identify compounds that disrupt normal target gene interactions. Compounds, which stimulate the activity of a variant NTE or mimic the activity of a non-functional variant are particularly useful in the treatment of neurological disorders (e.g., HSP).

In one embodiment, the invention provides assays for screening candidate or test compounds that are substrates of a NTE protein or polypeptide or a biologically active portion thereof. In another embodiment, the invention provides assays for screening candidate or test compounds that bind to or modulate the activity of a NTE protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckermann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

In one embodiment, an assay is a cell-based assay in which a cell that expresses a NTE protein or biologically active portion thereof is contacted with a test compound, and the ability of the test compound to modulate a NTE's activity is determined. Determining the ability of the test compound to modulate NTE activity can be accomplished by monitoring, for example, changes in enzymatic activity. The cell, for example, can be of mammalian origin.

The ability of the test compound to modulate NTE binding to a compound, e.g., a NTE substrate, can also be evaluated. This can be accomplished, for example, by coupling the compound, e.g., the substrate, with a radioisotope or enzymatic label such that binding of the compound, e.g., the substrate, to a NTE can be determined by detecting the labeled compound, e.g., substrate, in a complex.

Alternatively, a NTE is coupled with a radioisotope or enzymatic label to monitor the ability of a test compound to modulate NTE binding to a NTE substrate in a complex. For example, compounds (e.g., substrates) can be labeled with $^{125}I$, $^{35}S$ $^{14}C$ or $^3H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a NTE substrate) to interact with a NTE with or without the labeling of any of the interactants can be evaluated. For example, a microphysiometer can be used to detect the interaction of a compound with a NTE without the labeling of either the compound or the NTE (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and a NTE polypeptide.

In yet another embodiment, a cell-free assay is provided in which a NTE protein or biologically active portion thereof is contacted with a test compound and the ability of the test compound to bind to the NTE protein or biologically active portion thereof is evaluated. Preferred biologically active portions of NTE proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of a NTE protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize a NTE protein, an anti-NTE antibody or its target molecule to facilitate separation of complexed from non-complexed forms of one or both of the proteins, as well as to accommodate automation of the assay. Binding of a test compound to a NTE protein, or interaction of a NTE protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-NTE fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or NTE protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of NTE binding or activity determined using standard techniques. Other techniques for immobilizing either a NTE protein or a target molecule on matrices include using conjugation of biotin and streptavidin. Biotinylated NTE protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with NTE protein or target molecules but which do not interfere with binding of the NTE protein to its target molecule. Such antibodies can be derivatized to the wells of the plate, and unbound target or NTE protein trapped in the wells by antibody conjugation. Methods for detecting such complexes, in addition to those described above for the GST-immobilized complexes, include immudetection of complexes using antibodies reactive with the NTE protein or target molecule, as well as enzyme-linked assays which rely on detecting an enzymatic activity associated with the NTE protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. App 1 699:499-525 [1997]). Further, fluorescence energy transfer may also be conveniently utilized, as described herein, to detect binding without further purification of the complex from solution.

The assay can include contacting the NTE protein or biologically active portion thereof with a known compound that binds the NTE to form an assay mixture, contacting the assay mixture with a test compound, and determining the ability of the test compound to interact with a NTE protein, wherein determining the ability of the test compound to interact with a NTE protein includes determining the ability of the test compound to preferentially bind to NTE or biologically active portion thereof, or to modulate the activity of a target molecule, as compared to the known compound.

To the extent that a NTE can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, a NTE protein can be used as a "bait protein" in a two-hybrid assay or three-hybrid assay (see, e.g., U.S. Pat. No. 5,283, 317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent W0 94/10300; each of which is herein incorporated by reference), to identify other proteins, that bind to or interact with a NTE ("NTE-binding proteins" or "NTE-bp") and are involved in NTE activity. Such NTE-bps can be activators or inhibitors of signals by the NTE proteins or targets as, for example, downstream elements of a NTE-mediated signaling pathway.

Modulators of NTE expression can also be identified. For example, a cell or cell free mixture is contacted with a candidate compound and the expression of a NTE mRNA or protein evaluated relative to the level of expression of the NTE mRNA or protein in the absence of the candidate compound. When expression of the NTE mRNA or protein is greater in the presence of the candidate compound than in its absence, the candidate compound is identified as a stimulator of a NTE mRNA or protein expression. Alternatively, when expression of NTE mRNA or protein is less (i.e., statistically significantly less) in the presence of the candidate compound than in its absence, the candidate compound is identified as an inhibitor of NTE mRNA or protein expression. The level of NTE mRNA or protein expression can be determined by methods described herein for detecting NTE mRNA or protein.

A modulating agent can be identified using a cell-based or a cell free assay, and the ability of the agent to modulate the activity of a NTE protein can be confirmed in vivo, e.g., in an animal such as an animal model for a disease (e.g., an animal with an NTE related neurological disorder).

B. Therapeutic Agents

This invention further pertains to novel agents identified by the above-described screening assays. Accordingly, it is within the scope of this invention to further use an agent identified as described herein (e.g., a NTE modulating agent or mimetic, a NTE specific antibody, or a NTE-binding partner) in an appropriate animal model (such as those described herein) to determine the efficacy, toxicity, side effects, or mechanism of action, of treatment with such an agent. Furthermore, as described above, novel agents identified by the above-described screening assays can be, e.g., used for treatments of neurological disorders (e.g., including, but not limited to, motor neuron disorders). In some embodiments, the agents are NTE ligands or ligand analogs (e.g., identified using the drug screening methods described above).

VIII. Pharmaceutical Compositions Containing NTE Nucleic Acid, Peptides, and Analogs The present invention further provides pharmaceutical compositions which may comprise all or portions of NTE polynucleotide sequences, NTE polypeptides, inhibitors or antagonists of NTE bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by mutant NTE alleles (e.g., spastic paraplegia diseases). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, NTE nucleotide and NTE amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, NTE polynucleotide sequences or NTE amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton, Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of NTE may be that amount that suppresses spastic paraplegia related symptoms. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of NTE, conditions indicated on the label may include treatment of condition related to spastic paraplegia diseases.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts NTE levels.

A therapeutically effective dose refers to that amount of NTE that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.01 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for NTE than for the inhibitors of NTE. Administration to the bone marrow may necessitate delivery in a manner different from intravenous injections.

IX. Mutations Within the NTE Gene Result in Motor Neuron Disorders

Motor neuron disorders include amyotrophic lateral sclerosis, hereditary spastic paraplegia (HSP), primary lateral sclerosis, progressive pseudobulbar palsy, progressive muscular atrophy, progressive bulbar palsy, and postpolio syndrome. Motor neuron disorders typically involve progressive deterioration of the motor nerves in the spinal cord or brain, causing muscle weakness that can progress to paralysis.

NTE is an integral membrane protein present in all neurons and in some non-neural-cell types of vertebrates. NTE is involved in a cell-signaling pathway controlling interactions between neurons and accessory glial cells in the developing nervous system. NTE has serine esterase activity and efficiently catalyses the hydrolysis of phenyl valerate (PV) in vitro. By sequence analysis NTE is related neither to the major serince esterase family, which included acetylcholinesterase, nor to any other known serine hydrolases. NTE comprises at least two functional domains: an N-terminal putative regulatory domain and a C-terminal effector domain which contains the esterase activity and is, in part, conserved in proteins found in bacteria, yeast, nematodes and insects. NTE's effector domain contains three predicted transmembrane segments, and the active-site serine residue lies at the center of one of these segments. The isolated recombinant domain shows PV hydrolase activity only when incorporated into phospholipid liposomes.

Studies conducted in the course of the present invention indicate that motor neuron disorders are associated with mutations in the NTE gene (e.g., SEQ ID NOs: 2-4). In preferred embodiments, the present invention provides a method of diagnosing motor neuron disorders through genetic sequencing of a subject's NTE gene sequence. In other embodiments, the present invention provides a method of diagnosing motor neuron disorders through enzymatic testing of a subject's NTE enzyme. In other preferred embodiments, the risk of developing a motor neuron disorder may be ascertained through genetic testing of a subject's NTE gene sequence. In further embodiments, the risk of developing a motor neuron disorder may be ascertained through enzymatic testing of a subject's NTE enzyme.

X. Mutations Within NTE Gene Result in Susceptibility to Organophosphate Toxicity The present invention also provides methods for screening individuals for increased susceptibility to organophosphate toxicity. Many organophosphate compounds are neurotoxic. Organophosphate compounds include pesticides (e.g., disulfoton, phorate, dimethoate, ciodrin, dichlorvos, dioxathion, ruelene, carbophenothion, supona, hexaethyl tetraphosphate, tetraethyl pyrophosphate, octamethyl pyrophosphoramide, ethyl p-nitrophenyl thionobenzenephosphonate, parathion, malathion, ronnel, coumaphos, diazinon, trichlorfon, paraoxon, potasan, dimefox, mipafox, schradan, sevin, chlorpyrifos, dimeton) and chemical warfare agents (e.g., sarin, soman, tabun, cyclohexyl methylphosphonofluoridate, O-ethyl S-diisopropylaminomethyl methylphosphonothiolate).

Organophosphate compounds irreversibly bind to cholinesterase, causing the phosphorylation and deactivation of acetylcholinesterase. The subsequent accumulation of acetylcholine at the neural synapse causes an initial overstimulation, followed by eventual exhaustion and disruption of postsynaptic neural transmission in the central nervous system (CNS) and peripheral nervous systems (PNS). Typically, if the organophosphate/cholinesterase bond is not broken by pharmacologic intervention within 24 hours, large amounts of cholinesterase are destroyed, causing long-term morbidity or death.

The nicotinic (sympathomimetic) effects from accumulation of acetylcholine at motor end plates cause persistent depolarization of skeletal muscles, resulting in fasciculations, muscle weakness, hypertension, and tachycardia. Muscarinic effects from potentiation of postganglionic parasympathetic activity of smooth muscles may cause smooth muscle contractions in all organs (e.g., lung, GI, eye, bladder, secretory glands) and reduction of sinus node and AV conduction, causing bradyarrhythmias or resultant ventricular dysrhythmias. CNS effects may cause excessive stimulation (e.g., seizure), leading to depression and coma. Actual signs and symptoms depend on the balance between muscarinic and nicotinic receptors.

Treatment of organophosphate toxicity includes reducing excessive cholinergic levels. Anticholinergic agents (e.g., atropine, oximes, pralidoxime) cause pharmacologic antagonism of excess anticholinesterase activity at muscarinic receptors. Oximes reverse the inhibition of acetylcholinesterase and nicotinic effects, including muscle paralysis. Additional treatment of organophospate toxicity includes GI decontaminants (e.g., activated charcoal), antiseizure agents (e.g., benzodiazepines, diazepam, lorazepam, midazolam).

Individuals with altered NTE expression have increased susceptibility to organophosphate toxicity. Chemically or genetically induced NTE deficiency causes sensitivity to organophosphate toxicity and increases resulting neurotoxic symptoms (see Winrow et al., 33(4) Nature Genetics 477-485 (2003); herein incorporated by reference). Studies conducted during the course of the present invention indicate that individuals possessing an altered NTE gene sequence (e.g., SEQ ID NOs.: 2-4) have increased susceptibility to organophosphate toxicity and neurotoxicity.

In preferred embodiments, an individual is screened for increased susceptibility to organophosphate toxicity and neurotoxicity through genetic testing of the individual's NTE gene sequence. In other preferred embodiments, an individual is screened for increased susceptibility to organophosphate toxicity and neurotoxicity through enzymatic testing of the individual's NTE enzyme expression.

EXAMPLES

Example 1

Genome wide genetic linkage analysis utilizing the ABI Prism Marker Set MD10 was performed on a Venezuelan family afflicted with motor neuron disease. A genetic linkage between the motor neuron disease and a 1.9 cM locus on chromosome 19p13.3, a region containing NTE. Analysis of the NTE coding sequence showed that each affected subject was homozygous for, and each obligate carrier heterozygous, for a missense NTE mutation. The missense NTE mutation was a substitution of guanine for adenine at cDNA position 3034 (SEQ ID NO: 2). This mutation disrupted an inter-species conserved residue (M1012V) in the NTE active site.

Example 2

A second small kindred with Troyer syndrome was analyzed for linkage to chromosome 19 by examining 22 microsatellite markers on chromosome 19p. The analysis indicated linkage to chromosome 19. Analysis of the NTE coding sequencing showed that each affected subject and one parent contained a 4 bp insertion at position 2944 (SEQ ID NO: 3). The present invention is not limited to a particular mechanism. Indeed, an understanding of the mechanism is not necessary to practice the present invention. Nonetheless, based upon these results, it is expected that this 4 bp insertion at position 2944 leads to a truncated NTE protein of 1012 aa.

Example 3

Six entries in the NCBI database correspond to all or part of the NTE sequence. Five sequences contain an Adenine (abbreviated A) at NTE cDNA 2953. This encodes Lysine (abbreviated K) at amino acid position 985. One sequence contains Guanine (abbreviated G) at NTE cDNA 2953 (SEQ ID NO: 4). This encodes Arginine (abbreviated R) at amino acid position 985. DNA was sequenced from more than seven unrelated subjects and it was found that all had Adenine (A) at NTE cDNA 2953. The present invention is not limited to a particular mechanism. Indeed, an understanding of the mechanism is not necessary to practice the present invention. Nonetheless, it was concluded that NTE cDNA sequence is polymorphic at position 2953. Additionally, it was concluded that the most common sequence at this position is Adenine (A). Additionally, it was concluded that Guanine (G) at this position is a rare variant. It is noted that the respective amino acid encoded by this position is within the NTE esterase region. The present invention is not limited to a particular mechanism. Indeed, an understanding of the mechanism is not necessary to practice the present invention. Nonetheless, these results indicate that this polymorphism affects NTE function.

Example 4

A consanguineous family was studied in which affected subjects developed childhood onset insidiously progressive lower extremity spastic weakness and wasting of distal upper and lower extremity muscles. Clinical evaluation of these subjects revealed lower extremity spasticity, hyperreflexia, extensor plantar responses, and wasting of intrinsic muscles in the hand and distal lower extremities. The clinical phenotype conformed to Troyer syndrome. Electromyography and nerve conduction studies were consistent with motor axonopathy affecting upper and lower extremities. Electrophysiologic studies met diagnostic criteria for amyotrophic lateral sclerosis. The disorder in this family conformed to an autosomal recessive, upper and lower motor neuron disease in which hereditary spastic paraplegia is associated with distal muscle wasting.

Example 5

Two unrelated kindreds in which affected subjects exhibited autosomal recessive, slowly progressive lower extremity spastic weakness associated with wasting of distal upper and lower extremity muscles were evaluated. Subjects met clinical criteria for amyotrophic lateral sclerosis (ALS) and conformed to "Troyer syndrome." Magnetic resonance imaging demonstrated spinal cord atrophy and electromyography identified motor axonopathy. Genetic analysis of one consanguineous kindred suggested linkage between the disorder and a 22 cM locus on chromosome 19p13, a region containing NTE. Analysis of NTE's coding sequence in this family showed an M1O12V mutation disrupting an inter-species conserved residue in NTE's catalytic domain in both affected individuals but not unaffected individuals or 98 control subjects. Analysis of NTE's coding sequence in the second non-consanguinous kindred showed that affected subjects were compound heterozygotes for two NTE mutations: one allele had 2826A>G mutation which causes substitution of an inter-species conserved residue R890H in NTE's catalytic domain; the other allele had a 4 bp insertion (NTE mRNA position 3104) which causes protein truncation after residue 1020. These mutations were present separately in each carrier parent and absent in 98 control subjects.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for diagnosing a motor neuron disease associated with mutations in NTE nucleic acid of SEQ ID NO: 1 in a subject, comprising:

a) providing a biological sample from a subject, wherein said biological sample comprises a NTE nucleic acid; and b) detecting the presence of a variant NTE nucleic acid sequence selected from the group consisting of SEQ ID NOs: 2, 3 and 4 in said biological sample, wherein the presence of a variant NTE nucleic acid sequence selected from the group consisting of SEQ ID NOs: 2, 3 and 4 is diagnostic for the motor neuron disease.

* * * * *

UNITED STATES PATENT AND TRADEMARK OFFICE
CERTIFICATE OF CORRECTION

| | |
|---|---|
| PATENT NO. | : 7,384,748 B2 |
| APPLICATION NO. | : 11/301524 |
| DATED | : June 10, 2008 |
| INVENTOR(S) | : Fink et al. |

Page 1 of 1

It is certified that error appears in the above-identified patent and that said Letters Patent is hereby corrected as shown below:

Item (73) on the Title Page,

"(73) Assignee: The Regents of the University of Michigan, Ann Arbor, MI (US)"

should read:

--(73) Assignee: The Regents of the University of Michigan, Ann Arbor, MI (US), and The United States Government as represented by the Department of Veterans Affairs, Washington, D.C. (US)--

Signed and Sealed this
Twenty-first Day of February, 2012

David J. Kappos
*Director of the United States Patent and Trademark Office*

SEQUENCE LISTING

```
<160> NUMBER OF SEQ ID NOS: 6

<210> SEQ ID NO 1
<211> LENGTH: 4225
<212> TYPE: DNA
<213> ORGANISM: Homo sapiens

<400> SEQUENCE: 1
atggaggctc cgctgcaaac tggaatggtg cttggcgtga tgatcggggc cggagtggcg      60
gtggtggtca cggccgtgct catcctcctg gtggtgcgga ggctgcgagt gccaaaaacc     120
ccagccccgg atggcccccg gtatcggttc cggaagaggg acaaagtgct cttctatggc     180
cggaagatta tgcggaaggt gtcacaatcc acctcctccc tcgtggatac ctctgtctcc     240
gccacctccc ggccacgcat gaggaagaaa ctgaagatgc tcaacattgc caagaagatc     300
ctgcgcatcc agaaagagac gcccacgctg cagcggaagg agccccgcc cgcagtgcta     360 gaagctgacc tgaccgaggg cgacctggct aactcccatc tgccctctga agtgctttat     420
atgctcaaga acgtccgggt gctgggccac ttcgagaagc cactcttcct ggagctctgc     480
cgccacatgg tcttccagcg gctgggccag ggtgactacg tcttccggcc gggccagcca     540
gatgccagca tctacgtggt gcaggacggg ctgctggagc tctgtctgcc agggcctgac     600
```

```
gggaaggagt gtgtggtgaa ggaagtggtt cctggggaca gcgtcaacag ccttctcagc    660
atcctggatg tcatcaccgg tcaccagcat ccccagcgga ccgtgtctgc ccgggcggcc    720
cgggactcca cggtgctgcg cctgccggtg gaagcattct ccgcggtctt caccaagtac    780
ccggagagct tggtgcgggt cgtgcagatc atcatggtgc ggctgcagcg agtcaccttc    840
ctggcactgc acaactacct gggtctgacc aatgagctct tcagccacga gatccagccc    900
ctgcgtctgt tccccagccc cggcctccca actcgcacca gccctgtgcg gggctccaag    960
agaatggtca gcacctcagc tacagacgag cccagggaga ccccagggcg gccacccgat   1020
cccaccgggg ccccgctgcc tggacctaca ggggaccctg tgaagcccac atccctggaa   1080 acccccctcgc cccctctgct gagccgctgc gtctccatgc caggggacat ctcaggcttg   1140
cagggtggcc cccgctccga cttcgacatg gcctatgagc gtggccggat ctccgtgtcc   1200
ctgcaagaag aggcctccgg ggggtccctg gcagcccccg ctcggacccc cactcaggag   1260
cctcgtgagc agccggcagg cgcctgtgaa tacagctact gtgaggatga gtcggccact   1320
ggtggctgcc ctttcgggcc ctaccagggc cgccagacca gcagcatctt cgaggcagca   1380
aagcaggagc tggccaagct gatgcggatt gaggacccct ccctcctgaa cagcagagtc   1440
ttgctgcacc acgccaaagc tggcaccatc attgcccgcc agggagacca ggacgtgagc   1500
ctgcacttcg tgctctgggg ctgcctgcac gtgtaccagc gcatgatcga caaggcggag   1560
gacgtgtgcc tgttcgtagc gcagcccggg gaactggtgg gcagctggc ggtgctcact   1620 ggcgaacctc tcatcttcac actgcgagcc aacgcgact gcaccttcct gcggatctcc   1680
aagtccgact tctatgagat catgcgcgca cagcccagtg tggtgctgag tgcggcgcac   1740
acggtggcag ccaggatgtc gcccttcgtg cgccagatgg acttcgccat cgactggact   1800
gcagtggagg cgggacgcgc gctgtacagg cagggcgacc gctccgactg cacttacatc   1860
gtgctcaatg gcggctgcg tagcgtgatc cagcgaggca gtggcaagaa ggagctggtg   1920
ggcgagtacg gccgcggcga cctcatcggc gtggtggagg cactgacccg gcagccgcga   1980
gccacgacgg tgcacgcggt gcgcgacacg gagctggcca gcttcccga gggcaccttg   2040 ggtcacatca aacgccggta cccgcaggtc gtgacccgcc ttatccacct actgagccag   2100
aaaattctag ggaatttgca gcagctgcaa ggacccttcc cagcaggctc tgggttgggt   2160
gtgcccccac actcggaact caccaacccca gccagcaacc tggcaactgt ggcaatcctg   2220
cctgtgtgtg ctgaggtccc catggtggcc ttcacgctgg agctgcagca cgccctgcag   2280
gccatcggtc cgacgctact ccttaacagt gacatcatcc gggcacgcct gggggcctcc   2340
gcactggata gcatccaaga gttccggctg tcagggtggc tggcccagca ggaggatgca   2400
caccgtatcg tactctacca gacggacgcc tcgctgacgc cctggaccgt gcgctgcctg   2460
cgacaggccg actgcatcct cattgtgggc ctgggggacc aggagcctac cctcggccag   2520
ctggagcaga tgctggagaa cacggctgtg cgcgcccta gcagctagt cctgctccac   2580 cgagaggagg gcgcgggccc cacgcgcacc gtggagtggc taaatatgcg cagctggtgc   2640
tcggggcacc tgcacctgcg ctgtccgcgc cgcctctttt cgcgccgcag ccctgccaag   2700
ctgcatgagc tctacgagaa ggttttctcc aggcgcgcgg accggcacag cgacttctcc   2760
cgcttggcga gggtgctcac ggggaacacc attgcccttg tgctaggcgg gggcgggggcc   2820 agggctgct cgcacatcgg agtactaaag gcattagagg aggcggggt ccccgtggac   2880 ctggtgggcg gcacgtccat tggctctttc atcgagcgt tgtacgcgga ggagcgcagc   2940
gccagccgca cgaggcagcg ggcccgggag tgggccaaga gcatgacttc ggtgctggaa   3000
```

-continued

```
cctgtgttgg acctcacgta cccagtcacc tccatgttca ctgggtctgc ctttaaccgc    3060
agcatccatc gggtcttcca ggataagcag attgaggacc tgtggctgcc ttacttcaac    3120
gtgaccacag atatcaccgc ctcagccatg cgagtccaca aagatggctc cctgtggcgg    3180
tacgtgcgcg ccagcatgac gctgtcgggc tacctgcccc cgctgtgcga ccccaaggac    3240
gggcacctac tcatggatgg cggctacatc aacaatctgc cagcggacat cgcccgcagc    3300
atgggtgcca aaacggtcat cgccattgac gtggggagcc aggatgagac ggacctcagc    3360
acctacgggg acagcctgtc cggctggtgg ctgctgtgga gcggctgaa tccctgggct    3420
gacaaggtaa aggttccaga catggctgaa atccagtccc gcctggccta cgtgtcctgt    3480
gtgcggcagc tagaggttgt caagtccagc tcctactgcg agtacctgcg cccgcccatc    3540
gactgcttca agaccatgga ctttgggaag ttcgaccaga tctatgatgt gggctaccag    3600
tacgggaagg cggtgtttgg aggctggagc cgtggcaacg tcattgagaa aatgctcaca    3660
gaccggcggt ctacagacct taatgagagc cgccgtgcag acgtgcttgc cttcccaagc    3720
tctggcttca ctgacttggc agagattgtg tcccggattg agcccccac gagctatgtc    3780
tctgatggct gtgctgacgg agaggagtca gattgtctga cagagtatga ggaggacgcc    3840
ggacccgact gctcgaggga tgaaggggg tcccccgagg cgcaagccc cagcactgcc    3900
tccgagatgg aggaggagaa gtcgattctc cggcaacgac gctgtctgcc caggagccg    3960
cccggctcag ccacagatgc ctgaggacct cgacaggggt cacccctcc ctcccaccc    4020
tggactgggc tggggtggc cccgtggggg tagctcactc cccctcctgc tgctatgcct    4080
gtgaccccg cggcccacac actggactga cctgccctga gcggggatgc agtgttgcac    4140
tgatgacttg accagccct ccccaataa actcgcctct ggaaaaaaaa aaaaaaaaaa    4200
aaaaaaaaaa aaaaaaaaaa aaaaa                                         4225

<210> SEQ ID NO 2
<211> LENGTH: 4225
<212> TYPE: DNA
<213> ORGANISM: Homo sapiens

<400> SEQUENCE: 2
atggaggctc cgctgcaaac tggaatggtg cttggcgtga tgatcggggc cggagtggcg    60
gtggtggtca cggccgtgct catcctcctg gtggtgcgga ggctgcgagt gccaaaaacc    120
ccagccccgg atgccccccg gtatcggttc cggaagaggg acaaagtgct cttctatggc    180
cggaagatta tgcggaaggt gtcacaatcc acctcctccc tcgtggatac ctctgtctcc    240
gccacctccc ggccacgcat gaggaagaaa ctgaagatgc tcaacattgc caagaagatc    300
ctgcgcatcc agaaagagac gcccacgctg cagcggaagg agccccgcc cgcagtgcta    360
gaagctgacc tgaccgaggg cgacctggct aactcccatc tgccctctga agtgctttat    420
atgctcaaga acgtccgggt gctgggccac ttcgagaagc cactcttcct ggagctctgc    480
cgccacatgg tcttccagcg gctgggccag ggtgactacg tcttccggcc gggcagcca    540
gatgccagca tctacgtggt gcaggacggg ctgctggagc tctgtctgcc agggcctgac    600
gggaaggagt gtgtggtgaa ggaagtggtt cctggggaca cgtcaacag ccttctcagc    660
atcctggatg tcatcaccgg tcaccagcat ccccagcgga ccgtgtctgc ccgggcggcc    720
cgggactcca cggtgctgcg cctgccggtg gaagcattct ccgcggtctt caccaagtac    780
ccggagagct tggtgcgggt cgtgcagatc atcatggtg ggctgcagcg agtcaccttc    840
```

```
ctggcactgc acaactacct gggtctgacc aatgagctct tcagccacga gatccagccc    900
ctgcgtctgt tccccagccc cggcctccca actcgcacca gccctgtgcg gggctccaag    960
agaatggtca gcacctcagc tacagacgag cccagggaga ccccagggcg gccacccgat   1020
cccaccgggg ccccgctgcc tggacctaca ggggaccctg tgaagcccac atccctggaa   1080
accccctcgc cccctctgct gagccgctgc gtctccatgc caggggacat ctcaggcttg   1140
cagggtggcc cccgctccga cttcgacatg gcctatgagc gtggccggat ctccgtgtcc   1200
ctgcaagaag aggcctccgg ggggtccctg gcagcccccg ctcggacccc cactcaggag   1260
cctcgtgagc agccggcagg cgcctgtgaa tacagctact gtgaggatga gtcggccact   1320
ggtggctgcc ctttcgggcc ctaccagggc cgccagacca gcagcatctt cgaggcagca   1380
aagcaggagc tggccaagct gatgcggatt gaggaccccct ccctcctgaa cagcagagtc   1440
ttgctgcacc acgccaaagc tggcaccatc attgcccgcc agggagacca ggacgtgagc   1500
ctgcacttcg tgtctggggg ctgcctgcac gtgtaccagc gcatgatcga caaggcggag   1560
gacgtgtgcc tgttcgtagc gcagcccggg gaactggtgg ggcagctggc ggtgctcact   1620
ggcgaacctc tcatcttcac actgcgagcc caacgcgact gcaccttcct gcggatctcc   1680
aagtccgact tctatgagat catgcgcgca cagcccagtg tggtgctgag tgcggcgcac   1740
acggtggcag ccaggatgtc gcccttcgtg cgccagatgg acttcgccat cgactggact   1800
gcagtggagg cgggacgcgc gctgtacagg cagggcgacc gctccgactg cacttacatc   1860
gtgctcaatg gcggctgcg tagcgtgatc cagcgaggca gtggcaagaa ggagctggtg   1920
ggcgagtacg gccgcggcga cctcatcggc gtggtggagg cactgacccg gcagccgcga   1980
gccacgacgg tgcacgcggt gcgcgacacg gagctggcca gcttcccgga gggcaccttg   2040
ggtcacatca aacgccggta cccgcaggtc gtgacccgcc ttatccacct actgagccag   2100
aaaattctag ggaatttgca gcagctgcaa ggacccttcc cagcaggctc tgggttgggt   2160
gtgcccccac actcggaact caccaaccca gccagcaacc tggcaactgt ggcaatcctg   2220
cctgtgtgtg ctgaggtccc catggtggcc ttcacgctgg agctgcagca cgccctgcag   2280
gccatcggtc cgacgctact ccttaacagt gacatcatcc gggcacgcct gggggcctcc   2340
gcactggata gcatccaaga gttccggctg tcagggtggc tggcccagca ggaggatgca   2400
caccgtatcg tactctacca gacggacgcc tcgctgacgc cctggaccgt gcgctgcctg   2460
cgacaggccg actgcatcct cattgtgggc ctgggggacc aggagcctac cctcggccag   2520
ctggagcaga tgctggagaa cacggctgtg cgcgcccctta gcagctagt cctgctccac   2580
cgagaggagg gcgcgggccc cacgcgcacc gtggagtggc taaatatgcg cagctggtgc   2640
tcggggcacc tgcacctgcg ctgtccgcgc cgcctctttt cgcgccgcag ccctgccaag   2700
ctgcatgagc tctacgagaa ggttttctcc aggcgcgcgg accggcacag cgacttctcc   2760
cgcttggcga gggtgctcac ggggaacacc attgcccttg tgctaggcgg gggcggggcc   2820
aggggctgct cgcacatcgg agtactaaag gcattagagg aggcggggt ccccgtggac   2880
ctggtgggcg gcacgtccat tggctctttc atcggagcgt tgtacgcgga ggagcgcagc   2940
gccagccgca cgaggcagcg ggccgggag tgggccaaga gcatgacttc ggtgctggaa   3000
cctgtgttgg acctcacgta cccagtcacc tccgtgttca ctgggtctgc ctttaaccgc   3060
agcatccatc gggtcttcca ggataagcag attgaggacc tgtggctgcc ttacttcaac   3120
gtgaccacag atatcaccgc ctcagccatg cgagtccaca aagatggctc cctgtggcgg   3180
tacgtgcgcg ccagcatgac gctgtcgggc tacctgcccc cgctgtgcga ccccaaggac   3240
```

-continued

```
gggcacctac tcatggatgg cggctacatc aacaatctgc cagcggacat cgcccgcagc    3300
atgggtgcca aaacggtcat cgccattgac gtggggagcc aggatgagac ggacctcagc    3360
acctacgggg acagcctgtc cggctggtgg ctgctgtgga agcggctgaa tccctgggct    3420
gacaaggtaa aggttccaga catggctgaa atccagtccc gcctggccta cgtgtcctgt    3480
gtgcggcagc tagaggttgt caagtccagc tcctactgcg agtacctgcg cccgcccatc    3540
gactgcttca agaccatgga ctttgggaag ttcgaccaga tctatgatgt gggctaccag    3600
tacgggaagg cggtgtttgg aggctggagc cgtggcaacg tcattgagaa aatgctcaca    3660
gaccggcggt ctacagacct aatgagagc cgccgtgcag acgtgcttgc cttcccaagc    3720
tctggcttca ctgacttggc agagattgtg tcccggattg agccccccac gagctatgtc    3780
tctgatggct gtgctgacgg agaggagtca gattgtctga cagagtatga ggaggacgcc    3840
ggacccgact gctcgaggga tgaaggggg tcccccgagg gcgcaagccc cagcactgcc    3900
tccgagatgg aggaggagaa gtcgattctc cggcaacgac gctgtctgcc ccaggagccg    3960
cccggctcag ccacagatgc ctgaggacct cgacaggggt cacccctcc ctcccacccc    4020 tggactgggc tggggtggc ccgtggggg tagctcactc cccctcctgc tgctatgcct    4080 gtgaccccg cggcccacac actgactga cctgccctga gcggggatgc agtgttgcac    4140
tgatgacttg accagccct cccccaataa actcgcctct tggaaaaaaa aaaaaaaaa    4200 aaaaaaaaa aaaaaaaaa aaaaa                                          4225
```

<210> SEQ ID NO 3
<211> LENGTH: 4229
<212> TYPE: DNA
<213> ORGANISM: Homo sapiens

<400> SEQUENCE: 3

```
atggaggctc cgctgcaaac tggaatggtg cttggcgtga tgatcggggc cggagtggcg      60
gtggtggtca cggccgtgct catcctcctg gtggtgcgga ggctgcgagt gccaaaaacc     120
ccagccccgg atggccccg gtatcggttc cggaagaggg acaaagtgct cttctatggc     180
cggaagatta tgcggaaggt gtcacaatcc acctcctccc tcgtggatac ctctgtctcc     240
gccacctccc ggccacgcat gaggaagaaa ctgaagatgc tcaacattgc caagaagatc     300
ctgcgcatcc agaaagagac gcccacgctg cagcggaagg agcccccgcc cgcagtgcta     360
gaagctgacc tgaccgaggg cgacctggct aactcccatc tgccctctga agtgctttat     420
atgctcaaga acgtccgggt gctgggccac ttcgagaagc cactcttcct ggagctctgc     480
cgccacatgg tcttccagcg gctgggccag ggtgactacg tcttccggcc gggcagcca     540 gatgccagca tctacgtggt gcaggacggg ctgctggagc tctgtctgcc agggcctgac     600
gggaaggagt gtgtggtgaa ggaagtggtt cctggggaca cgtcaacag ccttctcagc     660 atcctggatg tcatcaccgg tcaccagcat ccccagcgga ccgtgtctgc ccgggcggcc     720
cgggactcca cggtgctgcg cctgccggtg gaagcattct ccgcggtctt caccaagtac     780
ccggagagct tggtgcgggt cgtgcagatc atcatggtgc ggctgcagcg agtcaccttc     840
ctggcactgc acaactacct gggtctgacc aatgagctct tcagccacga gatccagccc     900
ctgcgtctgt tccccagccc cggcctccca actcgcacca gccctgtgcg gggctccaag     960
agaatggtca gcacctcagc tacagacgag cccaggagag cccaggggcg gccacccgat    1020
cccaccgggg ccccgctgcc tggacctaca ggggaccctg tgaagcccac atccctggaa    1080
```

-continued

```
accccctcgc cccctctgct gagccgctgc gtctccatgc caggggacat ctcaggcttg      1140
cagggtggcc cccgctccga cttcgacatg gcctatgagc gtggccggat ctccgtgtcc      1200
ctgcaagaag aggcctccgg ggggtccctg gcagccccg ctcggacccc cactcaggag       1260
cctcgtgagc agccggcagg cgcctgtgaa tacagctact gtgaggatga gtcggccact      1320
ggtggctgcc ctttcgggcc ctaccagggc cgccagacca gcagcatctt cgaggcagca      1380
aagcaggagc tggccaagct gatgcggatt gaggaccccc ccctcctgaa cagcagagtc      1440
ttgctgcacc acgccaaagc tggcaccatc attgcccgcc agggagacca ggacgtgagc      1500
ctgcacttcg tgctctgggg ctgcctgcac gtgtaccagc gcatgatcga caaggcggag      1560
gacgtgtgcc tgttcgtagc gcagcccggg gaactggtgg ggcagctggc ggtgctcact      1620
ggcgaacctc tcatcttcac actgcgagcc caacgcgact gcaccttcct gcggatctcc      1680
aagtccgact tctatgagat catgcgcgca cagcccagtg tggtgctgag tgcggcgcac      1740
acggtggcag ccaggatgtc gcccttcgtg cgccagatgg acttcgccat cgactggact      1800
gcagtggagg cgggacgcgc gctgtacagg cagggcgacc gctccgactg cacttacatc      1860
gtgctcaatg gcggctgcg tagcgtgatc cagcgaggca gtggcaagaa ggagctggtg       1920
ggcgagtacg gccgcggcga cctcatcggc gtggtggagg cactgacccg gcagccgcga      1980
gccacgacgg tgcacgcggt gcgcgacacg gagctggcca gcttcccga gggcaccttg       2040 ggtcacatca aacgccggta cccgcaggtc gtgacccgcc ttatccacct actgagccag      2100
aaaattctag ggaatttgca gcagctgcaa ggacccttcc cagcaggctc tgggttgggt      2160
gtgcccccac actcggaact caccaaccca gccagcaacc tggcaactgt ggcaatcctg      2220
cctgtgtgtg ctgaggtccc catggtggcc ttcacgctgg agctgcagca cgccctgcag      2280
gccatcggtc cgacgctact ccttaacagt gacatcatcc gggcacgcct ggggccctcc      2340
gcactggata gcatccaaga gttccggctg tcagggtggc tggcccagca ggaggatgca      2400
caccgtatcg tactctacca gacggacgcc tcgctgacgc cctggaccgt gcgctgcctg      2460
cgacaggccg actgcatcct cattgtgggc ctggggacc aggagcctac cctcggccag       2520
ctggagcaga tgctggagaa cacggctgtg cgcgcccta agcagctagt cctgctccac       2580
cgagaggagg gcgcgggccc cacgcgcacc gtggagtggc taaatatgcg cagctggtgc      2640
tcggggcacc tgcacctgcg ctgtccgcgc cgcctctttt cgcgccgcag ccctgccaag      2700
ctgcatgagc tctacgagaa ggttttctcc aggcgcgcgg accggcacag cgacttctcc      2760
cgcttggcga gggtgctcac ggggaacacc attgcccttg tgctaggcgg gggcggggcc      2820
aggggctgct cgcacatcgg agtactaaag gcattagagg aggcgggggt ccccgtggac      2880
ctggtgggcg gcacgtccat ggctctttc atcggagcgt tgtacgcgga ggagcgcagc       2940
gccagccagc cgcacgaggc agcgggcccg ggagtgggcc aagagcatga cttcggtgct      3000
ggaacctgtg ttggacctca cgtacccagt cacctccatg ttcactgggt ctgccttaa       3060 ccgcagcatc catcgggtct tccaggataa gcagattgag gacctgtggc tgccttactt      3120
caacgtgacc acagatatca ccgcctcagc catgcgagtc cacaaagatg gctccctgtg      3180
gcggtacgtg cgcgccagca tgacgctgtc gggctacctg ccccgctgt gcgaccccaa       3240 ggacgggcac ctactcatgg atggcggcta catcaacaat ctgccagcgg acatcgcccg      3300
cagcatgggt gccaaaacgg tcatcgccat tgacgtgggg agccaggatg agacggacct      3360
cagcacctac ggggacagcc tgtccggctg gtggctgctg tggaagcggc tgaatccctg      3420
ggctgacaag gtaaaggttc cagacatggc tgaaatccag tcccgcctgg cctacgtgtc      3480
```

```
ctgtgtgcgg cagctagagg ttgtcaagtc cagctcctac tgcgagtacc tgcgcccgcc    3540
catcgactgc ttcaagacca tggactttgg gaagttcgac cagatctatg atgtgggcta    3600
ccagtacggg aaggcggtgt ttggaggctg agccgtggc aacgtcattg agaaaatgct     3660
cacagaccgg cggtctacag accttaatga gagccgccgt gcagacgtgc ttgccttccc    3720
aagctctggc ttcactgact tggcagagat tgtgtcccgg attgagcccc ccacgagcta    3780
tgtctctgat ggctgtgctg acggagagga gtcagattgt ctgacagagt atgaggagga    3840
cgccggaccc gactgctcga gggatgaagg ggggtccccc gagggcgcaa gccccagcac    3900
tgcctccgag atggaggagg agaagtcgat tctccggcaa cgacgctgtc tgccccagga    3960
gccgcccggc tcagccacag atgcctgagg acctcgacag gggtcacccc ctccctccca    4020
cccctggact gggctggggg tggccccgtg ggggtagctc actccccctc ctgctgctat    4080
gcctgtgacc cccgcggccc acacactgga ctgacctgcc ctgagcgggg atgcagtgtt    4140
gcactgatga cttgaccagc ccctccccca ataaactcgc ctcttggaaa aaaaaaaaa     4200 aaaaaaaaaa aaaaaaaaaa aaaaaaaaa                                      4229

<210> SEQ ID NO 4
<211> LENGTH: 4225
<212> TYPE: DNA
<213> ORGANISM: Homo sapiens

<400> SEQUENCE: 4
atggaggctc cgctgcaaac tggaatggtg cttggcgtga tgatcggggc cggagtggcg      60
gtggtggtca cggccgtgct catcctcctg gtggtgcgga ggctgcgagt gccaaaaacc     120
ccagcccccg atggccccg gtatcggttc cggaagaggg acaaagtgct cttctatggc     180
cggaagatta tgcggaaggt gtcacaatcc acctcctccc tcgtggatac ctctgtctcc     240
gccacctccc ggccacgcat gaggaagaaa ctgaagatgc tcaacattgc caagaagatc     300
ctgcgcatcc agaaagagac gcccacgctg cagcggaagg agcccccgcc cgcagtgcta     360
gaagctgacc tgaccgaggg cgacctggct aactcccatc tgccctctga agtgctttat     420
atgctcaaga acgtccgggt gctgggccac ttcgagaagc cactcttcct ggagctctgc     480
cgccacatgt tcttccagcg gctgggccag ggtgactacg tcttccggcc gggccagcca     540
gatgccagca tctacgtggt gcaggacggg ctgctggagc tctgtctgcc agggcctgac     600
gggaaggagt gtgtggtgaa ggaagtggtt cctgggggaca gcgtcaacag ccttctcagc     660
atcctggatg tcatcaccgg tcaccagcat ccccagcgga ccgtgtctgc ccgggcggcc     720
cgggactcca cggtgctgcg cctgccggtg gaagcattct ccgcggtctt caccaagtac     780
ccggagagct tggtgcgggt cgtgcagatc atcatggtgc ggctgcagcg agtcaccttc     840
ctggcactgc acaactacct gggtctgacc aatgagctct tcagccacga gatccagccc     900
ctgcgtctgt tccccagccc cggcctccca actcgcacca gccctgtgcg ggctccaag     960 agaatggtca gcacctcagc tacagacgag cccagggaga cccagggcg gccacccgat     1020 cccaccgggg cccgctgcc tggacctaca ggggacccctg tgaagcccac atccctggaa     1080 acccctcgc ccctctgct gagccgctgc gtctccatgc caggggacat ctcaggcttg     1140
cagggtggcc ccgctccga cttcgacatg gcctatgagc gtggcggat ctccgtgtcc     1200 ctgcaagaag aggcctccgg ggggtccctg gcagccccg ctcggacccc cactcaggag     1260
cctcgtgagc agccggcagg cgcctgtgaa tacagctact gtgaggatga gtcggccact     1320
```

```
ggtggctgcc ctttcgggcc ctaccagggc cgccagacca gcagcatctt cgaggcagca   1380
aagcaggagc tggccaagct gatgcggatt gaggaccect ccctcctgaa cagcagagtc   1440
ttgctgcacc acgccaaagc tggcaccatc attgcccgcc agggagacca ggacgtgagc   1500
ctgcacttcg tgctctgggg ctgcctgcac gtgtaccagc gcatgatcga caaggcggag   1560
gacgtgtgcc tgttcgtagc gcagcccggg gaactggtgg ggcagctggc ggtgctcact   1620
ggcgaacctc tcatcttcac actgcgagcc caacgcgact gcaccttcct gcggatctcc   1680
aagtccgact tctatgagat catgcgcgca cagcccagtg tggtgctgag tgcggcgcac   1740
acggtggcag ccaggatgtc gcccttcgtg cgccagatgg acttcgccat cgactggact   1800
gcagtggagg cgggacgcgc gctgtacagg cagggcgacc gctccgactg cacttacatc   1860
gtgctcaatg gcggctgcg tagcgtgatc cagcgaggca gtggcaagaa ggagctggtg   1920
ggcgagtacg gccgcggcga cctcatcggc gtggtggagg cactgacccg gcagccgcga   1980
gccacgacgg tgcacgcggt gcgcgacacg gagctggcca gcttcccgag ggcaccttg   2040 ggtcacatca aacgccggta cccgcaggtc gtgacccgcc ttatccacct actgagccag   2100
aaaattctag gaatttgca gcagctgcaa ggacccttcc cagcaggctc tgggttgggt   2160
gtgcccccac actcggaact caccaaccca gccagcaacc tggcaactgt ggcaatcctg   2220
cctgtgtgtg ctgaggtccc catggtggcc ttcacgctgg agctgcagca cgccctgcag   2280
gccatcggtc cgacgctact ccttaacagt gacatcatcc gggcacgcct gggggcctcc   2340
gcactggata gcatccaaga gttccggctg tcagggtggc tggcccagca ggaggatgca   2400
caccgtatcg tactctacca gacggacgcc tcgctgacgc cctggaccgt gcgctgcctg   2460
cgacaggccg actgcatcct cattgtgggc ctgggggacc aggagcctac cctcggccag   2520
ctggagcaga tgctggagaa cacggctgtg cgcgccctta gcagctagt cctgctccac   2580 cgagaggagg cgcgggccc cacgcgcacc gtggagtggc taaatatgcg cagctggtgc   2640
tcggggcacc tgcacctgcg ctgtccgcgc cgcctctttt cgcgccgcag ccctgccaag   2700
ctgcatgagc tctacgagaa ggttttctcc aggcgcgcgg accggcacag cgacttctcc   2760
cgcttggcga gggtgctcac ggggaacacc attgcccttg tgctaggcgg gggcggggcc   2820
aggggctgct cgcacatcgg agtactaaag gcattagagg aggcgggggt ccccgtggac   2880
ctggtgggcg gcacgtccat tggctctttc atcggagcgt tgtacgcgga ggagcgcagc   2940
gccagccgca cggggcagcg ggcccggag tgggccaaga gcatgacttc ggtgctggaa   3000
cctgtgttgg acctcacgta cccagtcacc tccatgttca ctgggtctgc ctttaaccgc   3060
agcatccatc gggtcttcca ggataagcag attgaggacc tgtggctgcc ttacttcaac   3120
gtgaccacag atatcaccgc ctcagccatg cgagtccaca aagatggctc cctgtggcgg   3180
tacgtgcgcg ccagcatgac gctgtcgggc tacctgcccc cgctgtgcga ccccaaggac   3240
gggcacctac tcatggatgg cggctacatc aacaatctgc agcggacat cgcccgcagc   3300 atgggtgcca aaacggtcat cgccattgac gtggggagcc aggatgagac ggacctcagc   3360
acctacgggg acagcctgtc cggctggtgg ctgctgtgga gcggctgaa tccctgggct   3420 gacaaggtaa aggttccaga catggctgaa atccagtccc gcctggccta cgtgtcctgt   3480
gtgcggcagc tagaggttgt caagtccagc tcctactgcg agtacctgcg cccgcccatc   3540
gactgcttca agaccatgga ctttgggaag ttcgaccaga tctatgatgt gggctaccag   3600
tacgggaagg cggtgtttgg aggctggagc cgtggcaacg tcattgagaa aatgctcaca   3660
gaccggcggt ctacagacct taatgagagc cgccgtgcag acgtgcttgc cttcccaagc   3720
```

-continued

```
tctggcttca ctgacttggc agagattgtg tcccggattg agccccccac gagctatgtc   3780
tctgatggct gtgctgacgg agaggagtca gattgtctga cagagtatga ggaggacgcc   3840
ggacccgact gctcgaggga tgaagggggg tcccccgagg gcgcaagccc cagcactgcc   3900
tccgagatgg aggaggagaa gtcgattctc cggcaacgac gctgtctgcc ccaggagccg   3960
cccggctcag ccacagatgc ctgaggacct cgacagggt cacccccctcc ctcccacccc   4020 tggactgggc tggggtggc cccgtggggg tagctcactc ccctcctgc tgctatgcct    4080 gtgaccccg cggcccacac actggactga cctgccctga gcggggatgc agtgttgcac   4140
tgatgacttg accagcccct cccccaataa actcgcctct tggaaaaaaa aaaaaaaaa    4200 aaaaaaaaa aaaaaaaaaa aaaaa                                          4225
```

<210> SEQ ID NO 5
<211> LENGTH: 1402
<212> TYPE: PRT
<213> ORGANISM: Homo sapiens
<220> FEATURE:
<221> NAME/KEY: NON_CONS
<222> LOCATION: (1327)..(1328)
<220> FEATURE:
<221> NAME/KEY: NON_CONS
<222> LOCATION: (1349)..(1350)
<220> FEATURE:
<221> NAME/KEY: NON_CONS
<222> LOCATION: (1367)..(1368)
<220> FEATURE:
<221> NAME/KEY: NON_CONS
<222> LOCATION: (1377)..(1378)
<220> FEATURE:
<221> NAME/KEY: NON_CONS
<222> LOCATION: (1384)..(1385)

<400> SEQUENCE: 5

```
Met Glu Ala Pro Leu Gln Thr Gly Met Val Leu Gly Val Met Ile Gly
 1               5                  10                  15

Ala Gly Val Ala Val Val Val Thr Ala Val Leu Ile Leu Leu Val Val
            20                  25                  30

Arg Arg Leu Arg Val Pro Lys Thr Pro Ala Pro Asp Gly Pro Arg Tyr
        35                  40                  45

Arg Phe Arg Lys Arg Asp Lys Val Leu Phe Tyr Gly Arg Lys Ile Met
    50                  55                  60

Arg Lys Val Ser Gln Ser Thr Ser Ser Leu Val Asp Thr Ser Val Ser
65                  70                  75                  80

Ala Thr Ser Arg Pro Arg Met Arg Lys Lys Leu Lys Met Leu Asn Ile
                85                  90                  95

Ala Lys Lys Ile Leu Arg Ile Gln Lys Glu Thr Pro Thr Leu Gln Arg
            100                 105                 110

Lys Glu Pro Pro Pro Ala Val Leu Glu Ala Asp Leu Thr Glu Gly Asp
        115                 120                 125

Leu Ala Asn Ser His Leu Pro Ser Glu Val Leu Tyr Met Leu Lys Asn
    130                 135                 140

Val Arg Val Leu Gly His Phe Glu Lys Pro Leu Phe Leu Glu Leu Cys
145                 150                 155                 160

Arg His Met Val Phe Gln Arg Leu Gly Gln Gly Asp Tyr Val Phe Arg
                165                 170                 175

Pro Gly Gln Pro Asp Ala Ser Ile Tyr Val Val Gln Asp Gly Leu Leu
            180                 185                 190

Glu Leu Cys Leu Pro Gly Pro Asp Gly Lys Glu Cys Val Val Lys Glu
```

-continued

```
            195                 200                 205
Val Val Pro Gly Asp Ser Val Asn Ser Leu Leu Ser Ile Leu Asp Val
210                 215                 220
Ile Thr Gly His Gln His Pro Gln Arg Thr Val Ser Ala Arg Ala Ala
225                 230                 235                 240
Arg Asp Ser Thr Val Leu Arg Leu Pro Val Glu Ala Phe Ser Ala Val
                245                 250                 255
Phe Thr Lys Tyr Pro Glu Ser Leu Val Arg Val Val Gln Ile Ile Met
                260                 265                 270
Val Arg Leu Gln Arg Val Thr Phe Leu Ala Leu His Asn Tyr Leu Gly
                275                 280                 285
Leu Thr Asn Glu Leu Phe Ser His Glu Ile Gln Pro Leu Arg Leu Phe
290                 295                 300
Pro Ser Pro Gly Leu Pro Thr Arg Thr Ser Pro Val Arg Gly Ser Lys
305                 310                 315                 320
Arg Met Val Ser Thr Ser Ala Thr Asp Glu Pro Arg Glu Thr Pro Gly
                325                 330                 335
Arg Pro Pro Asp Pro Thr Gly Ala Pro Leu Pro Gly Pro Thr Gly Asp
                340                 345                 350
Pro Val Lys Pro Thr Ser Leu Glu Thr Pro Ser Pro Leu Leu Ser
                355                 360                 365
Arg Cys Val Ser Met Pro Gly Asp Ile Ser Gly Leu Gln Gly Gly Pro
                370                 375                 380
Arg Ser Asp Phe Asp Met Ala Tyr Glu Arg Gly Arg Ile Ser Val Ser
385                 390                 395                 400
Leu Gln Glu Glu Ala Ser Gly Gly Ser Leu Ala Ala Pro Ala Arg Thr
                405                 410                 415
Pro Thr Gln Glu Pro Arg Glu Gln Pro Ala Gly Ala Cys Glu Tyr Ser
                420                 425                 430
Tyr Cys Glu Asp Glu Ser Ala Thr Gly Gly Cys Pro Phe Gly Pro Tyr
                435                 440                 445
Gln Gly Arg Gln Thr Ser Ser Ile Phe Glu Ala Ala Lys Gln Glu Leu
                450                 455                 460
Ala Lys Leu Met Arg Ile Glu Asp Pro Ser Leu Leu Asn Ser Arg Val
465                 470                 475                 480
Leu Leu His His Ala Lys Ala Gly Thr Ile Ile Ala Arg Gln Gly Asp
                485                 490                 495
Gln Asp Val Ser Leu His Phe Val Leu Trp Gly Cys Leu His Val Tyr
                500                 505                 510
Gln Arg Met Ile Asp Lys Ala Glu Asp Val Cys Leu Phe Val Ala Gln
                515                 520                 525
Pro Gly Glu Leu Val Gly Gln Leu Ala Val Leu Thr Gly Glu Pro Leu
530                 535                 540
Ile Phe Thr Leu Arg Ala Gln Arg Asp Cys Thr Phe Leu Arg Ile Ser
545                 550                 555                 560
Lys Ser Asp Phe Tyr Glu Ile Met Arg Ala Gln Pro Ser Val Val Leu
                565                 570                 575
Ser Ala Ala His Thr Val Ala Ala Arg Met Ser Pro Phe Val Arg Gln
                580                 585                 590
Met Asp Phe Ala Ile Asp Trp Thr Ala Val Glu Ala Gly Arg Ala Leu
                595                 600                 605
Tyr Arg Gln Gly Asp Arg Ser Asp Cys Thr Tyr Ile Val Leu Asn Gly
610                 615                 620
```

-continued

```
Arg Leu Arg Ser Val Ile Gln Arg Gly Ser Gly Lys Lys Glu Leu Val
625                 630                 635                 640

Gly Glu Tyr Gly Arg Gly Asp Leu Ile Gly Val Val Glu Ala Leu Thr
            645                 650                 655

Arg Gln Pro Arg Ala Thr Thr Val His Ala Val Arg Asp Thr Glu Leu
            660                 665                 670

Ala Lys Leu Pro Glu Gly Thr Leu Gly His Ile Lys Arg Arg Tyr Pro
            675                 680                 685

Gln Val Val Thr Arg Leu Ile His Leu Leu Ser Gln Lys Ile Leu Gly
        690                 695                 700

Asn Leu Gln Gln Leu Gln Gly Pro Phe Pro Ala Gly Ser Gly Leu Gly
705                 710                 715                 720

Val Pro Pro His Ser Glu Leu Thr Asn Pro Ala Ser Asn Leu Ala Thr
                725                 730                 735

Val Ala Ile Leu Pro Val Cys Ala Glu Val Pro Met Val Ala Phe Thr
                740                 745                 750

Leu Glu Leu Gln His Ala Leu Gln Ala Ile Gly Pro Thr Leu Leu Leu
                755                 760                 765

Asn Ser Asp Ile Ile Arg Ala Arg Leu Gly Ala Ser Ala Leu Asp Ser
770                 775                 780

Ile Gln Glu Phe Arg Leu Ser Gly Trp Leu Ala Gln Gln Glu Asp Ala
785                 790                 795                 800

His Arg Ile Val Leu Tyr Gln Thr Asp Ala Ser Leu Thr Pro Trp Thr
                805                 810                 815

Val Arg Cys Leu Arg Gln Ala Asp Cys Ile Leu Ile Val Gly Leu Gly
                820                 825                 830

Asp Gln Glu Pro Thr Leu Gly Gln Leu Glu Gln Met Leu Glu Asn Thr
                835                 840                 845

Ala Val Arg Ala Leu Lys Gln Leu Val Leu Leu His Arg Glu Gly
                850                 855                 860

Ala Gly Pro Thr Arg Thr Val Glu Trp Leu Asn Met Arg Ser Trp Cys
865                 870                 875                 880

Ser Gly His Leu His Leu Arg Cys Pro Arg Arg Leu Phe Ser Arg Arg
                885                 890                 895

Ser Pro Ala Lys Leu His Glu Leu Tyr Glu Lys Val Phe Ser Arg Arg
                900                 905                 910

Ala Asp Arg His Ser Asp Phe Ser Arg Leu Ala Arg Val Leu Thr Gly
                915                 920                 925

Asn Thr Ile Ala Leu Val Leu Gly Gly Gly Ala Arg Gly Cys Ser
930                 935                 940

His Ile Gly Val Leu Lys Ala Leu Glu Glu Ala Gly Val Pro Val Asp
945                 950                 955                 960

Leu Val Gly Gly Thr Ser Ile Gly Ser Phe Ile Gly Ala Leu Tyr Ala
                965                 970                 975

Glu Glu Arg Ser Ala Ser Arg Thr Arg Gln Arg Ala Arg Glu Trp Ala
                980                 985                 990

Lys Ser Met Thr Ser Val Leu Glu Pro Val Leu Asp Leu Thr Tyr Pro
            995                 1000                1005

Val Thr Ser Met Phe Thr Gly Ser Ala Phe Asn Arg Ser Ile His
        1010                1015                1020

Arg Val Phe Gln Asp Lys Gln Ile Glu Asp Leu Trp Leu Pro Tyr
        1025                1030                1035
```

-continued

```
Phe Asn Val Thr Thr Asp Ile Thr Ala Ser Ala Met Arg Val His
    1040                1045                1050

Lys Asp Gly Ser Leu Trp Arg Tyr Val Arg Ala Ser Met Thr Leu
    1055                1060                1065

Ser Gly Tyr Leu Pro Pro Leu Cys Asp Pro Lys Asp Gly His Leu
    1070                1075                1080

Leu Met Asp Gly Gly Tyr Ile Asn Asn Leu Pro Ala Asp Ile Ala
    1085                1090                1095

Arg Ser Met Gly Ala Lys Thr Val Ile Ala Ile Asp Val Gly Ser
    1100                1105                1110

Gln Asp Glu Thr Asp Leu Ser Thr Tyr Gly Asp Ser Leu Ser Gly
    1115                1120                1125

Trp Trp Leu Leu Trp Lys Arg Leu Asn Pro Trp Ala Asp Lys Val
    1130                1135                1140

Lys Val Pro Asp Met Ala Glu Ile Gln Ser Arg Leu Ala Tyr Val
    1145                1150                1155

Ser Cys Val Arg Gln Leu Glu Val Val Lys Ser Ser Ser Tyr Cys
    1160                1165                1170

Glu Tyr Leu Arg Pro Pro Ile Asp Cys Phe Lys Thr Met Asp Phe
    1175                1180                1185

Gly Lys Phe Asp Gln Ile Tyr Asp Val Gly Tyr Gln Tyr Gly Lys
    1190                1195                1200

Ala Val Phe Gly Gly Trp Ser Arg Gly Asn Val Ile Glu Lys Met
    1205                1210                1215

Leu Thr Asp Arg Arg Ser Thr Asp Leu Asn Glu Ser Arg Arg Ala
    1220                1225                1230

Asp Val Leu Ala Phe Pro Ser Ser Gly Phe Thr Asp Leu Ala Glu
    1235                1240                1245

Ile Val Ser Arg Ile Glu Pro Pro Thr Ser Tyr Val Ser Asp Gly
    1250                1255                1260

Cys Ala Asp Gly Glu Glu Ser Asp Cys Leu Thr Glu Tyr Glu Glu
    1265                1270                1275

Asp Ala Gly Pro Asp Cys Ser Arg Asp Glu Gly Gly Ser Pro Glu
    1280                1285                1290

Gly Ala Ser Pro Ser Thr Ala Ser Glu Met Glu Glu Glu Lys Ser
    1295                1300                1305

Ile Leu Arg Gln Arg Arg Cys Leu Pro Gln Glu Pro Pro Gly Ser
    1310                1315                1320

Ala Thr Asp Ala Gly Pro Arg Gln Gly Ser Pro Pro Ser His
    1325                1330                1335

Pro Trp Thr Gly Leu Gly Val Ala Pro Trp Gly Leu Thr Pro Pro
    1340                1345                1350

Pro Ala Ala Met Pro Val Thr Pro Ala Ala His Thr Leu Asp Pro
    1355                1360                1365

Ala Leu Ser Gly Asp Ala Val Leu His Leu Asp Gln Pro Leu Pro
    1370                1375                1380

Gln Thr Arg Leu Leu Glu Lys Lys Lys Lys Lys Lys Lys Lys Lys
    1385                1390                1395

Lys Lys Lys Lys
    1400

<210> SEQ ID NO 6
<211> LENGTH: 1402
<212> TYPE: PRT
```

```
<213> ORGANISM: Homo sapiens
<220> FEATURE:
<221> NAME/KEY: NON_CONS
<222> LOCATION: (1327)..(1328)
<220> FEATURE:
<221> NAME/KEY: NON_CONS
<222> LOCATION: (1349)..(1350)
<220> FEATURE:
<221> NAME/KEY: NON_CONS
<222> LOCATION: (1367)..(1368)
<220> FEATURE:
<221> NAME/KEY: NON_CONS
<222> LOCATION: (1371)..(1372)
<220> FEATURE:
<221> NAME/KEY: NON_CONS
<222> LOCATION: (1384)..(1385)

<400> SEQUENCE: 6

Met Glu Ala Pro Leu Gln Thr Gly Met Val Leu Gly Val Met Ile Gly
1               5                   10                  15

Ala Gly Val Ala Val Val Thr Ala Val Leu Ile Leu Leu Val Val
                20                  25                  30

Arg Arg Leu Arg Val Pro Lys Thr Pro Ala Pro Asp Gly Pro Arg Tyr
        35                  40                  45

Arg Phe Arg Lys Arg Asp Lys Val Leu Phe Tyr Gly Arg Lys Ile Met
    50                  55                  60

Arg Lys Val Ser Gln Ser Thr Ser Ser Leu Val Asp Thr Ser Val Ser
65                  70                  75                  80

Ala Thr Ser Arg Pro Arg Met Arg Lys Lys Leu Lys Met Leu Asn Ile
                85                  90                  95

Ala Lys Lys Ile Leu Arg Ile Gln Lys Glu Thr Pro Thr Leu Gln Arg
            100                 105                 110

Lys Glu Pro Pro Pro Ala Val Leu Glu Ala Asp Leu Thr Glu Gly Asp
        115                 120                 125

Leu Ala Asn Ser His Leu Pro Ser Glu Val Leu Tyr Met Leu Lys Asn
    130                 135                 140

Val Arg Val Leu Gly His Phe Glu Lys Pro Leu Phe Leu Glu Leu Cys
145                 150                 155                 160

Arg His Met Val Phe Gln Arg Leu Gly Gln Gly Asp Tyr Val Phe Arg
                165                 170                 175

Pro Gly Gln Pro Asp Ala Ser Ile Tyr Val Val Gln Asp Gly Leu Leu
            180                 185                 190

Glu Leu Cys Leu Pro Gly Pro Asp Gly Lys Glu Cys Val Val Lys Glu
        195                 200                 205

Val Val Pro Gly Asp Ser Val Asn Ser Leu Leu Ser Ile Leu Asp Val
    210                 215                 220

Ile Thr Gly His Gln His Pro Gln Arg Thr Val Ser Ala Arg Ala Ala
225                 230                 235                 240

Arg Asp Ser Thr Val Leu Arg Leu Pro Val Glu Ala Phe Ser Ala Val
                245                 250                 255

Phe Thr Lys Tyr Pro Glu Ser Leu Val Arg Val Val Gln Ile Ile Met
            260                 265                 270

Val Arg Leu Gln Arg Val Thr Phe Leu Ala Leu His Asn Tyr Leu Gly
        275                 280                 285

Leu Thr Asn Glu Leu Phe Ser His Glu Ile Gln Pro Leu Arg Leu Phe
    290                 295                 300

Pro Ser Pro Gly Leu Pro Thr Arg Thr Ser Pro Val Arg Gly Ser Lys
305                 310                 315                 320
```

-continued

```
Arg Met Val Ser Thr Ser Ala Thr Asp Glu Pro Arg Glu Thr Pro Gly
                325                 330                 335

Arg Pro Pro Asp Pro Thr Gly Ala Pro Leu Pro Gly Pro Thr Gly Asp
            340                 345                 350

Pro Val Lys Pro Thr Ser Leu Glu Thr Pro Ser Pro Leu Leu Ser
        355                 360                 365

Arg Cys Val Ser Met Pro Gly Asp Ile Ser Gly Leu Gln Gly Gly Pro
    370                 375                 380

Arg Ser Asp Phe Asp Met Ala Tyr Glu Arg Gly Arg Ile Ser Val Ser
385                 390                 395                 400

Leu Gln Glu Glu Ala Ser Gly Ser Leu Ala Ala Pro Ala Arg Thr
                405                 410                 415

Pro Thr Gln Glu Pro Arg Glu Gln Pro Ala Gly Ala Cys Glu Tyr Ser
                420                 425                 430

Tyr Cys Glu Asp Glu Ser Ala Thr Gly Gly Cys Pro Phe Gly Pro Tyr
    435                 440                 445

Gln Gly Arg Gln Thr Ser Ser Ile Phe Glu Ala Ala Lys Gln Glu Leu
    450                 455                 460

Ala Lys Leu Met Arg Ile Glu Asp Pro Ser Leu Leu Asn Ser Arg Val
465                 470                 475                 480

Leu Leu His His Ala Lys Ala Gly Thr Ile Ile Ala Arg Gln Gly Asp
                485                 490                 495

Gln Asp Val Ser Leu His Phe Val Leu Trp Gly Cys Leu His Val Tyr
            500                 505                 510

Gln Arg Met Ile Asp Lys Ala Glu Asp Val Cys Leu Phe Val Ala Gln
        515                 520                 525

Pro Gly Glu Leu Val Gly Gln Leu Ala Val Leu Thr Gly Glu Pro Leu
    530                 535                 540

Ile Phe Thr Leu Arg Ala Gln Arg Asp Cys Thr Phe Leu Arg Ile Ser
545                 550                 555                 560

Lys Ser Asp Phe Tyr Glu Ile Met Arg Ala Gln Pro Ser Val Val Leu
                565                 570                 575

Ser Ala Ala His Thr Val Ala Ala Arg Met Ser Pro Phe Val Arg Gln
            580                 585                 590

Met Asp Phe Ala Ile Asp Trp Thr Ala Val Glu Ala Gly Arg Ala Leu
        595                 600                 605

Tyr Arg Gln Gly Asp Arg Ser Asp Cys Thr Tyr Ile Val Leu Asn Gly
    610                 615                 620

Arg Leu Arg Ser Val Ile Gln Arg Gly Ser Gly Lys Lys Glu Leu Val
625                 630                 635                 640

Gly Glu Tyr Gly Arg Gly Asp Leu Ile Gly Val Val Glu Ala Leu Thr
                645                 650                 655

Arg Gln Pro Arg Ala Thr Thr Val His Ala Val Arg Asp Thr Glu Leu
            660                 665                 670

Ala Lys Leu Pro Glu Gly Thr Leu Gly His Ile Lys Arg Arg Tyr Pro
        675                 680                 685

Gln Val Val Thr Arg Leu Ile His Leu Leu Ser Gln Lys Ile Leu Gly
    690                 695                 700

Asn Leu Gln Gln Leu Gln Gly Pro Phe Pro Ala Gly Ser Gly Leu Gly
705                 710                 715                 720

Val Pro Pro His Ser Glu Leu Thr Asn Pro Ala Ser Asn Leu Ala Thr
                725                 730                 735

Val Ala Ile Leu Pro Val Cys Ala Glu Val Pro Met Val Ala Phe Thr
```

-continued

```
                740                 745                 750
Leu Glu Leu Gln His Ala Leu Gln Ala Ile Gly Pro Thr Leu Leu Leu
            755                 760                 765
Asn Ser Asp Ile Ile Arg Ala Arg Leu Gly Ala Ser Ala Leu Asp Ser
            770                 775                 780
Ile Gln Glu Phe Arg Leu Ser Gly Trp Leu Ala Gln Gln Glu Asp Ala
785             790                 795                 800
His Arg Ile Val Leu Tyr Gln Thr Asp Ala Ser Leu Thr Pro Trp Thr
                805                 810                 815
Val Arg Cys Leu Arg Gln Ala Asp Cys Ile Leu Ile Val Gly Leu Gly
            820                 825                 830
Asp Gln Glu Pro Thr Leu Gly Gln Leu Glu Gln Met Leu Glu Asn Thr
            835                 840                 845
Ala Val Arg Ala Leu Lys Gln Leu Val Leu Leu His Arg Glu Glu Gly
            850                 855                 860
Ala Gly Pro Thr Arg Thr Val Glu Trp Leu Asn Met Arg Ser Trp Cys
865             870                 875                 880
Ser Gly His Leu His Leu Arg Cys Pro Arg Arg Leu Phe Ser Arg Arg
                885                 890                 895
Ser Pro Ala Lys Leu His Glu Leu Tyr Glu Lys Val Phe Ser Arg Arg
            900                 905                 910
Ala Asp Arg His Ser Asp Phe Ser Arg Leu Ala Arg Val Leu Thr Gly
            915                 920                 925
Asn Thr Ile Ala Leu Val Leu Gly Gly Gly Ala Arg Gly Cys Ser
            930                 935                 940
His Ile Gly Val Leu Lys Ala Leu Glu Glu Ala Gly Val Pro Val Asp
945             950                 955                 960
Leu Val Gly Gly Thr Ser Ile Gly Ser Phe Ile Gly Ala Leu Tyr Ala
                965                 970                 975
Glu Glu Arg Ser Ala Ser Arg Thr Arg Gln Arg Ala Arg Glu Trp Ala
            980                 985                 990
Lys Ser Met Thr Ser Val Leu Glu Pro Val Leu Asp Leu Thr Tyr Pro
            995                 1000                1005
Val Thr Ser Val Phe Thr Gly Ser Ala Phe Asn Arg Ser Ile His
    1010                1015                1020
Arg Val Phe Gln Asp Lys Gln Ile Glu Asp Leu Trp Leu Pro Tyr
    1025                1030                1035
Phe Asn Val Thr Thr Asp Ile Thr Ala Ser Ala Met Arg Val His
    1040                1045                1050
Lys Asp Gly Ser Leu Trp Arg Tyr Val Arg Ala Ser Met Thr Leu
    1055                1060                1065
Ser Gly Tyr Leu Pro Pro Leu Cys Asp Pro Lys Asp Gly His Leu
    1070                1075                1080
Leu Met Asp Gly Gly Tyr Ile Asn Asn Leu Pro Ala Asp Ile Ala
    1085                1090                1095
Arg Ser Met Gly Ala Lys Thr Val Ile Ala Ile Asp Val Gly Ser
    1100                1105                1110
Gln Asp Glu Thr Asp Leu Ser Thr Tyr Gly Asp Ser Leu Ser Gly
    1115                1120                1125
Trp Trp Leu Leu Trp Lys Arg Leu Asn Pro Trp Ala Asp Lys Val
    1130                1135                1140
Lys Val Pro Asp Met Ala Glu Ile Gln Ser Arg Leu Ala Tyr Val
    1145                1150                1155
```

-continued

```
Ser Cys Val Arg Gln Leu Glu Val Val Lys Ser Ser Ser Tyr Cys
    1160             1165             1170

Glu Tyr Leu Arg Pro Pro Ile Asp Cys Phe Lys Thr Met Asp Phe
    1175             1180             1185

Gly Lys Phe Asp Gln Ile Tyr Asp Val Gly Tyr Gln Tyr Gly Lys
    1190             1195             1200

Ala Val Phe Gly Gly Trp Ser Arg Gly Asn Val Ile Glu Lys Met
    1205             1210             1215

Leu Thr Asp Arg Arg Ser Thr Asp Leu Asn Glu Ser Arg Arg Ala
    1220             1225             1230

Asp Val Leu Ala Phe Pro Ser Ser Gly Phe Thr Asp Leu Ala Glu
    1235             1240             1245

Ile Val Ser Arg Ile Glu Pro Pro Thr Ser Tyr Val Ser Asp Gly
    1250             1255             1260

Cys Ala Asp Gly Glu Glu Ser Asp Cys Leu Thr Glu Tyr Glu Glu
    1265             1270             1275

Asp Ala Gly Pro Asp Cys Ser Arg Asp Glu Gly Gly Ser Pro Glu
    1280             1285             1290

Gly Ala Ser Pro Ser Thr Ala Ser Glu Met Glu Glu Glu Lys Ser
    1295             1300             1305

Ile Leu Arg Gln Arg Arg Cys Leu Pro Gln Glu Pro Pro Gly Ser
    1310             1315             1320

Ala Thr Asp Ala Gly Pro Arg Gln Gly Ser Pro Pro Pro Ser His
    1325             1330             1335

Pro Trp Thr Gly Leu Gly Val Ala Pro Trp Gly Leu Thr Pro Pro
    1340             1345             1350

Pro Ala Ala Met Pro Val Thr Pro Ala Ala His Thr Leu Asp Pro
    1355             1360             1365

Ala Leu Ser Gly Asp Ala Val Leu His Leu Asp Gln Pro Leu Pro
    1370             1375             1380

Gln Thr Arg Leu Leu Glu Lys Lys Lys Lys Lys Lys Lys Lys Lys
    1385             1390             1395

Lys Lys Lys Lys
    1400
```